(12) United States Patent
Chin

(10) Patent No.: US 7,264,587 B2
(45) Date of Patent: Sep. 4, 2007

(54) ENDOSCOPIC SUBXIPHOID SURGICAL PROCEDURES

(75) Inventor: Albert K Chin, Palo Alto, CA (US)

(73) Assignee: Origin Medsystems, Inc., Natick, MA (US)

( * ) Notice: Subject to any disclaimer, the term of this patent is extended or adjusted under 35 U.S.C. 154(b) by 867 days.

(21) Appl. No.: 10/346,663

(22) Filed: Jan. 17, 2003

(65) Prior Publication Data

US 2004/0111101 A1   Jun. 10, 2004

Related U.S. Application Data

(63) Continuation-in-part of application No. 10/347,212, filed on Jan. 17, 2003, which is a continuation-in-part of application No. 10/174,454, filed on Jun. 17, 2002, which is a continuation-in-part of application No. 10/140,309, filed on May 6, 2002, which is a continuation of application No. 09/635,721, filed on Aug. 9, 2000, application No. 10/346,663, which is a continuation-in-part of application No. 09/779,715, filed on Feb. 8, 2001, now Pat. No. 6,569,082, which is a continuation of application No. 09/738,608, filed on Dec. 14, 2000, now abandoned, which is a continuation-in-part of application No. 09/635,345, filed on Aug. 9, 2000, application No. 10/346,663, which is a continuation-in-part of application No. 10/006,321, filed on Dec. 4, 2001, now Pat. No. 6,706,052, which is a continuation of application No. 09/915,695, filed on Jul. 25, 2001, now Pat. No. 6,428,556.

(60) Provisional application No. 60/148,130, filed on Aug. 10, 1999, provisional application No. 60/150,737, filed on Aug. 25, 1999.

(51) Int. Cl.
*A61F 2/00* (2006.01)
*A61F 2/24* (2006.01)

(52) U.S. Cl. ....................................................... 600/37
(58) Field of Classification Search .................. 600/37, 600/16–18, 508
See application file for complete search history.

(56) References Cited

U.S. PATENT DOCUMENTS 207,932 A    9/1878   Alvord (Continued)

FOREIGN PATENT DOCUMENTS

DE    39 42 589    12/1989

(Continued)

OTHER PUBLICATIONS

International Search Report and Written Opinion, PCT/US04/00760, Jul. 6, 2005.

(Continued)

*Primary Examiner*—Charles A. Marmor, II
*Assistant Examiner*—Christine Hopkins
(74) *Attorney, Agent, or Firm*—Fenwick & West LLP

(57) ABSTRACT

Endoscopic subxiphoid surgical procedures and instruments facilitate translumination of tissue through the pericardium, and promote encircling an intrapericardial region with one or more tissue-ablating probes for ablating cardiac tissue substantially encircling the left and right pulmonary veins as a treatment for chronic atrial fibrillation. Such endoscopic subxiphoid surgical procedures and instruments also facilitate placement of epicardial tacks about the annulus of the mitral valve for supporting a tensioned suture or band that decreases the size of the mitral annulus to repair a regurgitant valve. Suction-oriented instruments facilitate temporary attachment to an organ to establish precise positioning on the organ during a surgical procedure.

3 Claims, 18 Drawing Sheets

U.S. PATENT DOCUMENTS

| | | |
|---|---|---|
| 1,727,495 A | 9/1929 | Wappler |
| 1,867,624 A | 7/1932 | Hoffman |
| 2,011,169 A | 8/1935 | Wappler |
| 2,028,635 A | 1/1936 | Wappler |
| 2,316,297 A | 4/1943 | Southerland et al. |
| 2,868,206 A | 1/1959 | Stoesser |
| 2,944,552 A | 7/1960 | Cannon |
| 3,185,155 A | 5/1965 | Slaten et al. |
| 3,338,916 A | 8/1967 | Edlich |
| 3,357,433 A | 12/1967 | Fourestier et al. |
| 3,856,016 A | 12/1974 | Davis |
| 3,870,048 A | 3/1975 | Yoon |
| 3,882,854 A | 5/1975 | Hulka et al. |
| 3,920,024 A | 11/1975 | Bowers |
| 3,934,115 A | 1/1976 | Peterson |
| RE29,088 E | 12/1976 | Shaw |
| 4,022,191 A | 5/1977 | Jamshidi |
| 4,181,123 A | 1/1980 | Crosby |
| 4,235,246 A | 11/1980 | Weiss |
| 4,270,549 A | 6/1981 | Heilman |
| 4,271,839 A | 6/1981 | Fogarty et al. |
| 4,291,707 A | 9/1981 | Heilman et al. |
| 4,318,410 A | 3/1982 | Chin |
| 4,319,562 A | 3/1982 | Crosby |
| 4,479,497 A | 10/1984 | Fogarty et al. |
| 4,493,711 A | 1/1985 | Chin et al. |
| 4,526,175 A | 7/1985 | Chin et al. |
| 4,630,609 A | 12/1986 | Chin |
| 4,662,371 A | 5/1987 | Whipple et al. |
| 4,765,341 A | 8/1988 | Mower et al. |
| 4,779,611 A | 10/1988 | Grooters et al. |
| 4,784,133 A | 11/1988 | Mackin |
| 4,863,440 A | 9/1989 | Chin |
| 4,921,483 A | 5/1990 | Wijay et al. |
| 4,991,578 A | 2/1991 | Cohen |
| 5,071,428 A | 12/1991 | Chin et al. |
| 5,129,394 A | 7/1992 | Mehra |
| 5,143,082 A | 9/1992 | Kindberg et al. |
| 5,150,706 A | 9/1992 | Cox et al. |
| 5,163,949 A | 11/1992 | Bonutti |
| 5,183,464 A | 2/1993 | Dubrul et al. |
| 5,215,521 A | 6/1993 | Cochran et al. |
| 5,246,014 A | 9/1993 | Williams et al. |
| 5,256,132 A | 10/1993 | Snyders |
| 5,271,380 A | 12/1993 | Riek et al. |
| 5,318,589 A | 6/1994 | Lichtman |
| 5,331,975 A | 7/1994 | Bonutti |
| 5,334,150 A | 8/1994 | Kaali |
| 5,336,252 A | 8/1994 | Cohen |
| 5,373,840 A | 12/1994 | Knighton |
| 5,376,076 A | 12/1994 | Kaali |
| 5,397,304 A | 3/1995 | Truckai |
| 5,433,198 A | 7/1995 | Desai |
| 5,437,680 A | 8/1995 | Yoon |
| 5,464,447 A | 11/1995 | Fogarty et al. |
| 5,496,345 A | 3/1996 | Kieturakis et al. |
| 5,514,153 A | 5/1996 | Bonutti |
| 5,540,711 A | 7/1996 | Kieturakis et al. |
| 5,551,947 A | 9/1996 | Kaali |
| 5,569,183 A | 10/1996 | Kieturakis |
| 5,569,291 A | 10/1996 | Privitera et al. |
| 5,569,292 A | 10/1996 | Scwemberger et al. |
| 5,571,161 A | 11/1996 | Starksen |
| 5,591,192 A | 1/1997 | Privitera et al. |
| 5,601,576 A | 2/1997 | Garrison |
| 5,601,589 A | 2/1997 | Fogarty et al. |
| 5,607,441 A | 3/1997 | Sierocuk et al. |
| 5,613,947 A | 3/1997 | Chin |
| 5,618,287 A | 4/1997 | Fogarty et al. |
| 5,630,813 A | 5/1997 | Kieturakis |
| 5,653,722 A | 8/1997 | Kieturakis |
| 5,653,726 A | 8/1997 | Kieturakis |
| 5,667,520 A | 9/1997 | Bonutti |
| 5,669,927 A | 9/1997 | Boebel et al. |
| 5,685,820 A | 11/1997 | Riek et al. |
| 5,690,648 A | 11/1997 | Fogarty et al. |
| 5,695,504 A | 12/1997 | Gifford, III et al. |
| 5,702,343 A | 12/1997 | Alferness |
| 5,702,417 A | 12/1997 | Hermann |
| 5,713,950 A * | 2/1998 | Cox ......................... 128/898 |
| 5,716,392 A | 2/1998 | Bourgeois et al. |
| 5,722,977 A | 3/1998 | Wilhelmy |
| 5,728,148 A | 3/1998 | Bostrom et al. |
| 5,730,756 A | 3/1998 | Kieturakis |
| 5,738,628 A | 4/1998 | Sierocuk et al. |
| 5,755,764 A | 5/1998 | Schreippel |
| 5,755,765 A | 5/1998 | Hyde et al. |
| 5,762,604 A | 6/1998 | Kieturakis |
| 5,772,680 A | 6/1998 | Kieturakis et al. |
| 5,797,946 A | 8/1998 | Chin |
| 5,800,449 A | 9/1998 | Wales |
| 5,810,878 A | 9/1998 | Burel et al. |
| 5,860,997 A | 1/1999 | Bonutti |
| 5,897,586 A | 4/1999 | Molina |
| 5,902,331 A | 5/1999 | Bonner et al. |
| 5,904,711 A | 5/1999 | Flom et al. |
| 5,972,020 A | 10/1999 | Carpentier et al. |
| 5,980,548 A | 11/1999 | Evans et al. |
| 6,007,546 A | 12/1999 | Snow et al. |
| 6,010,531 A * | 1/2000 | Donlon et al. ............... 623/2.1 |
| 6,036,714 A | 3/2000 | Chin |
| 6,039,748 A | 3/2000 | Savage et al. |
| 6,048,337 A | 4/2000 | Svedman |
| 6,068,621 A | 5/2000 | Balceta et al. |
| 6,095,968 A | 8/2000 | Snyders |
| 6,096,064 A | 8/2000 | Routh |
| 6,102,046 A | 8/2000 | Weinstein et al. |
| 6,126,590 A | 10/2000 | Alferness |
| 6,132,456 A | 10/2000 | Sommer et al. |
| 6,156,009 A | 12/2000 | Grabek |
| 6,162,195 A | 12/2000 | Igo et al. |
| 6,165,183 A * | 12/2000 | Kuehn et al. ................ 606/139 |
| 6,206,004 B1 | 3/2001 | Schmidt et al. |
| 6,267,763 B1 | 7/2001 | Castro |
| 6,287,250 B1 * | 9/2001 | Peng et al. .................... 600/37 |
| 6,322,536 B1 | 11/2001 | Rosengart et al. |
| 6,428,556 B1 | 8/2002 | Chin |
| 6,463,332 B1 | 10/2002 | Aldrich |
| 6,488,689 B1 | 12/2002 | Kaplan et al. |
| 6,569,082 B1 | 5/2003 | Chin |
| 6,607,547 B1 | 8/2003 | Chin |
| 6,612,978 B2 | 9/2003 | Lau et al. |
| 6,689,048 B2 | 2/2004 | Vanden Hoek et al. |
| 6,697,677 B2 | 2/2004 | Dahl et al. |
| 6,702,732 B1 | 3/2004 | Lau et al. |
| 6,706,052 B1 | 3/2004 | Chin |
| 6,835,193 B2 | 12/2004 | Epstein et al. |
| 6,889,091 B2 | 5/2005 | Hine et al. |
| 2002/0035361 A1 | 3/2002 | Houser et al. |
| 2002/0052602 A1 | 5/2002 | Wang et al. |
| 2002/0058925 A1 | 5/2002 | Kaplan et al. |
| 2002/0111637 A1 | 8/2002 | Kaplan et al. |
| 2002/0173622 A1 | 11/2002 | Wettstein et al. |
| 2002/0177207 A1 | 11/2002 | Sugiyama et al. |
| 2003/0212446 A1 | 11/2003 | Kaplan et al. |

FOREIGN PATENT DOCUMENTS

| | | |
|---|---|---|
| EP | 0095727 A1 | 7/1983 |
| EP | 0 642 764 | 9/1994 |
| EP | 0791330 A2 | 8/1997 |
| FR | 1 370580 | 8/1964 |
| GB | 2 082 459 | 8/1981 |
| GB | 2 195 540 | 9/1987 |

| | | |
|---|---|---|
| SU | 510235 | 4/1976 |
| SU | 1371689 | 3/1986 |
| WO | WO 96/32882 | 10/1996 |
| WO | WO97/26831 | 7/1997 |
| WO | WO 98/24488 A2 | 11/1998 |
| WO | WO 98/24488 A3 | 11/1998 |

OTHER PUBLICATIONS

Myers, E. L. et al., "Tsg101, an Inactive Homologue of Ubiquitin Ligase E2, Interacts Specifically With Human Immunodeficiency Virus Type 2 Gag Polyprotein and Results in Increased Levels of Ubiquinated Gag," J. Virol, Nov. 2002, vol. 76, No. 22.

International Search Report and Written Opinion, PCT/US04/00859, Jun. 20, 2005.

Bernhard, Victor M. et al., "Cardiovascular Endoscopy: Historical Perspectives", Endovascular Surgery, 1989 W.B. Saunders Company, pp. 13-30.

Broadman, R. et al., "ICD Implantation via Thoracoscopy, "Mailslot" Thoracotomy, and Subxiphoid Incision," The Annals of Thoracic Surgery, vol. 57, No. 2, Feb. 1994, pp. 475-476.

Carpentier, A., "Technique d'implantation de pace-maker par une voie d'abord abdominale sous-xyphoidienne," La Presse Medicate, Masson et Cle, Editeurs, Paris, vol. 76, No. 2, Jan. 13, 1968, 2 pp.

De Feyter, P.J. et al., "Permanent Cardiac Pacing with Sutureless Myocardial Electrodes: Experience In First One Hundred Patients," PACE, vol. 3, No. 2, Mar. 1980, pp. 144-149.

Delaria, G.A. et al., "Leg Wound Complications Associated With Coronary Revascularization", J. Thorac, Cardiovasc. Surgery, 81:403-407, 1981.

Dimitri, W.R., et al., "A Quick and Atraumatic Method of Autologous Vein Harvesting Using the Subcutaneous Extraluminal Dissector", J. Cardiovasc. Surg., 28:103-11, 1987.

Fogarty, M.D., Thomas J., et al., "Selected Applications of Balloon Dissection", pp. 45-52.

Hauer, G., et al. "Endoscopic Subfascial Discussion of Perforating Vein", Surg. Endos. 2:5-12, 1988.

"Incision Decision", Atrium Medical Corporation advertisement, appearing in J. Thorac. Cardiovasc. Surg. 83(4), 1982.

Meldrum-Hanna, W. et al., "Long Saphenous Vein Harvesting," J. Surg, 56: 923-924, 1986.

Moazami, N., M.D. et al., "Minimally Invasive Greater Saphenous Vein Harvesting For Coronary Artery Bypass Surgery", Mar. 1997, pp. 94-98.

Rashid, A., et al., "Subcutaneous Technique for Saphenous Vein Harvest", Ann. Thorac. Surg., 37(2):169-170, 1984.

"Saphenous Vein Grafts Are No. 1. Period," Atrium Medical Corporation advertisement, appearing in J. Thorac. Cardiovas. Surg., 82(6), 1981.

Stewart, S., M.D., "Placement of the Sutureless Epicardial Pacemaker Lead by the Subxiphoid Approach," The Annals of Thoracic Surgery, vol. 18, No. 3, Sep. 1974, pp. 308-313.

Watkins, Jr., L., M.D. et al., "Implantation of the Automatic Defibrillator: The Subxiphoid Approach," The Annals of Thoracic Surgery, vol. 34, No. 5, Nov. 1982, pp. 515-520.

Wheatley, D.J., M.D., ed., "Surgery of Coronary Artery Disease", C.V. Mosby Company, pp. 348-349, pp. 374-375.

Zenati M., M.D. et al., "Left Heart Pacing Lead Implantation Using Subxiphoid Videopericardioscopy," J. Cardiovasc Electrophysiol, vol. 14, Sep. 2003, pp. 949-963.

PCT International Search Report and Written Opinion, PCT/US04/00760, Sep. 27, 2006, 7 pages.

PCT International Search Report and Written Opinion; PCT/US04/34538, Nov. 3, 2005, 10 pages.

* cited by examiner

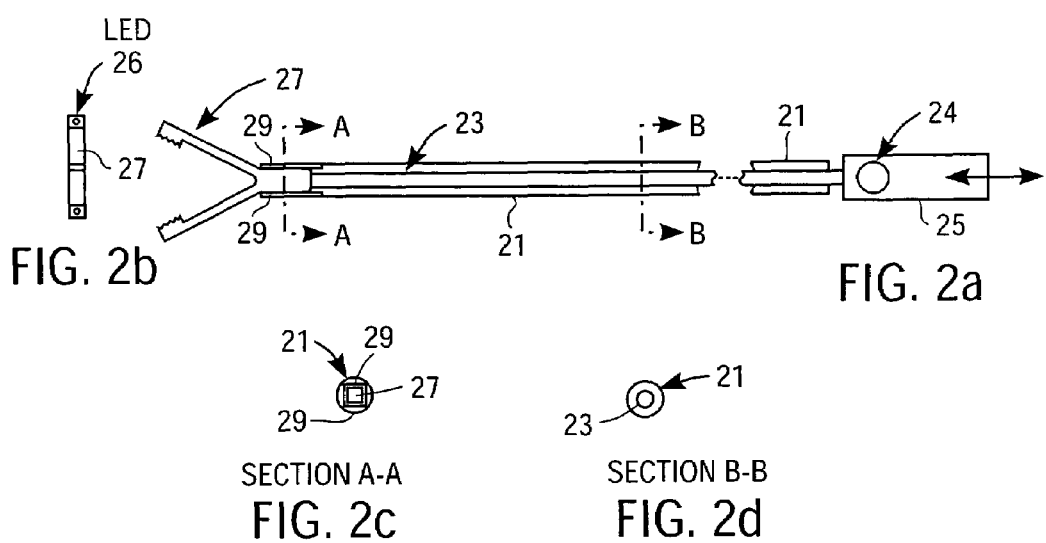
FIG. 2b  FIG. 2a
SECTION A-A
FIG. 2c
SECTION B-B
FIG. 2d
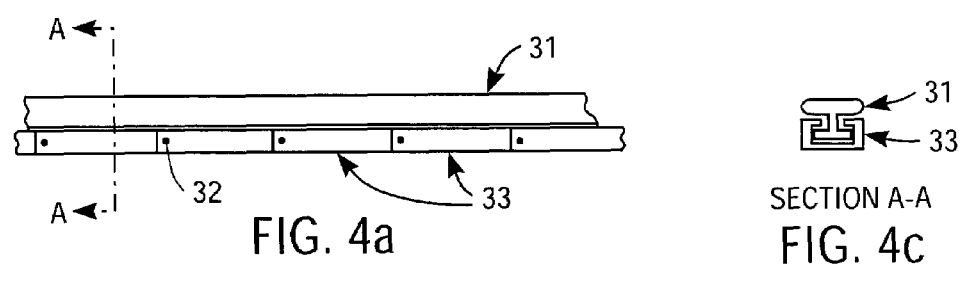
FIG. 4a
SECTION A-A
FIG. 4c
FIG. 4b
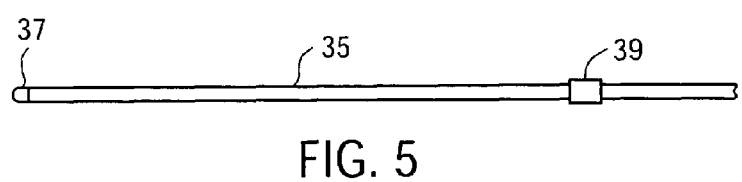
FIG. 5

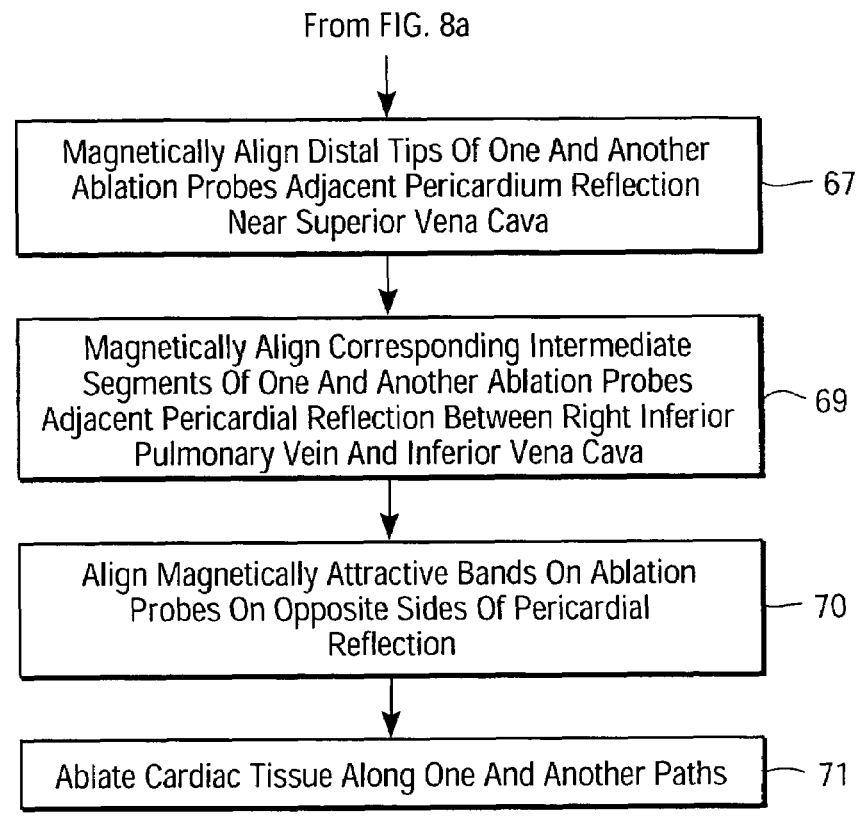

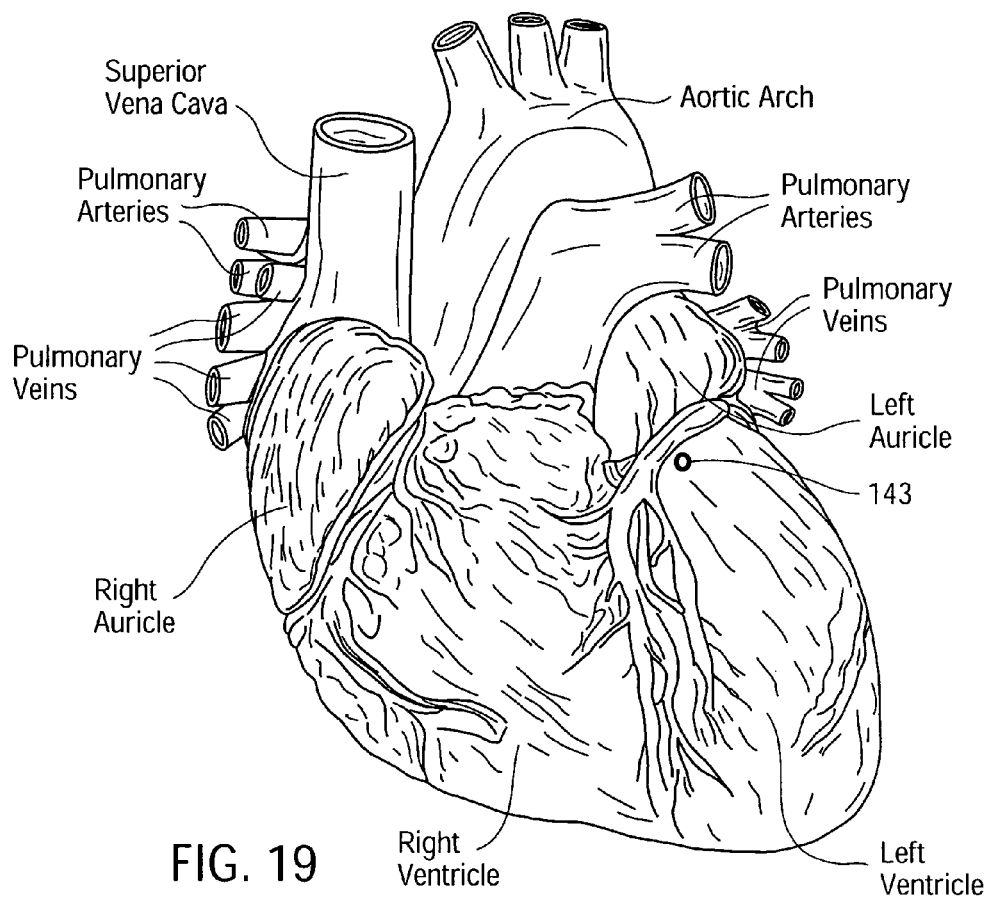
FIG. 19
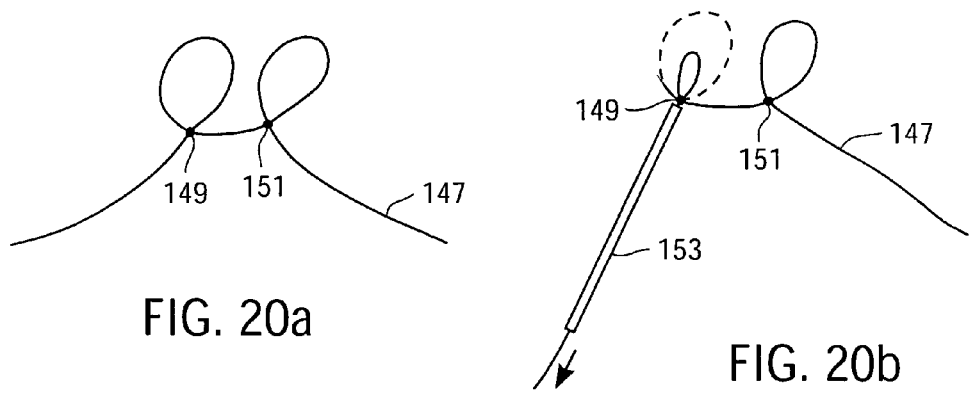
FIG. 20a
FIG. 20b

ENDOSCOPIC SUBXIPHOID SURGICAL PROCEDURES

RELATED APPLICATIONS

This is a continuation-in-part application of pending application Ser. No. 10/347,212, entitled "Apparatus and Methods for Endoscopic Surgical Procedures", filed on Jan. 17, 2003 by Albert K. Chin, which is a continuation-in-part application of pending application Ser. No. 10/174,454, entitled "Releasable Guide And Method For Endoscopic Cardiac Lead Placement", filed on Jun. 17, 2002 by Albert K. Chin, which is a continuation-in-part of pending application Ser. No. 10/140,309 entitled "Methods And Apparatus For Endoscopic Cardiac Surgery", filed on May 6, 2002 by Albert K. Chin, et al., which is a continuation of pending application Ser. No. 09/635,721 entitled "Apparatus For Endoscopic Access", filed on Aug. 9, 2000, which claims the benefit of provisional applications Ser. No. 60/148,130 filed on Aug. 10, 1999 and Ser. No. 60/150,737 filed on Aug. 25, 1999. This application is also a continuation-in-part application Ser. No. 09/779,715 entitled "Apparatus And Methods For Cardiac Restraint", filed on Feb. 8, 2001 by Albert K. Chin, now issued as U.S. Pat. No. 6,569,082 on May 27, 2003, which is a continuation of pending application Ser. No. 09/738,608 entitled "Apparatus And Methods For Cardiac Restraint", filed on Dec. 14, 2000 by Albert K. Chin, now abandoned, which is a continuation-in-part of pending application Ser. No. 09/635,345, entitled "Apparatus And Method For Subxiphoid Endoscopic Access", filed on Aug. 9, 2000 by Albert K. Chin, which claims the benefit of the aforecited provisional applications. This application is also a continuation-in-part of pending application Ser. No. 10/006,321 entitled "Longitudinal Dilator and Method", filed on Dec. 4, 2001 by Albert K. Chin, which issued as U.S. Pat. No. 6,706,052 on Mar. 16, 2004, and which is a continuation of application Ser. No. 09/915,695 entitled "Longitudinal Dilator And Method", filed on Jul. 25, 2001 by Albert K. Chin and now issued as U.S. Pat. No. 6,428,556, which claims the benefit of the aforecited provisional application Ser. No. 60/150,737, filed on Aug. 25, 1999, which applications are incorporated herein in their entireties by these references to form a part hereof.

FIELD OF THE INVENTION

This invention relates to endoscopic surgical procedures and more particularly to epicardial ablation of atrial tissue to treat chronic atrial fibrillation, and to surgical instruments and access procedures for surrounding the pulmonary veins at their sites of entry into the left atrium as targeted for tissue ablation, or for installing epicardial tacks and tensioning the epicardium between tacks to correct mitral valve regurgitation due to annular dilation.

BACKGROUND OF THE INVENTION

In one aspect of the present invention, tissue surrounding the pulmonary vein ostia is ablated at the site in the intrapericardial space where the veins enter into the left atrium as a clinically recognized treatment for chronic atrial fibrillation. Cardiac surgeons have been entering the chest through a standard sternotomy, dissecting a tract under the superior vena cava and the inferior vena cava, and threading an ablation probe around the four pulmonary veins. The probe enters posterior to the superior vena cava, winds through the transverse sinus of the pericardium, loops around the four pulmonary veins, and exits the tract that was dissected posterior to the inferior vena cava. The tract formed posterior to the superior vena cava enters into the transverse sinus of the pericardium. The tract formed posterior to the inferior vena cava completes the path of the ablation probe around the pulmonary veins.

In order to perform the above described probe placement endoscopically, one endoscopic cannula is advanced through a thoracotomy incision, or other entry incision, into the intrapericardial space adjacent the superior vena cava, and a second endoscopic cannula is inserted into the right pleural cavity via another thoracotomy incision. This latter endoscopic cannula in the right pleural cavity is used to dissect through the right medial pleural and the pericardium posterior to the superior vena cava, guided by transillumination light emitted by the other endoscopic cannula.

This technique uses two endoscopes, and two full sets of endoscopic equipment, including endoscope, video camera, light source, video monitor and light cable. The physical space occupied by two sets of endoscopic equipment is cumbersome in the operating room, and the expense is prohibitive to hospitals. Therefore, it is desirable to perform the procedure using one set of endoscopic equipment and one endoscopic cannula.

In other types of surgical procedures, various operative techniques have been suggested for repairing regurgitant mitral valves, including surgical placement of a closed or open ring at the mitral annulus to correct a dilated annulus causing regurgitation through the valve. A "bowtie" stitch placed across the mitral orifice may reform a large orifice into two smaller openings and decrease mitral regurgitation. Alternatively, intravascular repairs include insertion of a stent or spring into the coronary sinus to reshape the mitral annulus by placing such a preformed structure into the heart's venous system.

SUMMARY OF THE INVENTION

In accordance with one embodiment of the present invention an endoscopic cannula is used to enter the pericardium from a subxiphoid approach, visualize the superior vena cava, and place an illuminated clip on the pericardium adjacent the superior vena cava. The clip, as shown in FIGS. 2a-d, contains an attached light emitting diode (LED) that emits light from the tip of the clip. The endoscopic subxiphoid cannula is used to visualize the inferior vena cava, and a light emitting clip is attached to the pericardium adjacent the inferior vena cava. In another embodiment, an elongated light 'stick' can have a distal end positioned adjacent the inferior vena cava, and a second endoscope can be guided toward the position of the first source of light. The subxiphoid endoscopic cannula is then removed from the mediastinum and inserted into the right pleural cavity through a small thoracotomy incision. The transilluminating light from each clip guides the tissue-dissecting cannula during dissection under the superior and inferior vena cava, respectively. Dissection is performed via a combination of blunt dissection with a transparent tapered tip of the cannula, and dissection with the pericardial entry instrument.

Following dissection posterior to the inferior vena cava and dissection posterior to the superior vena cava, a flexible elongated probe or a flexible tubular sheath is used to encircle the pulmonary veins. The probe or sheath starts in the right pleural cavity, tracks posterior to the superior vena cava, then tracks along the transverse sinus superior to the right and left superior pulmonary veins, then inferior to the left and right inferior pulmonary veins, and posterior to the inferior vena cava, back out into the right pleural cavity. An ablation probe is advanced along the dissected path and energy is applied to ablate atrial tissue surrounding the pulmonary veins.

In accordance with another embodiment of the present invention, two probes may be advanced along the posterior pericardial surface around different courses to substantially encircle the four pulmonary veins, with the tips of the probes separated by a reflection (i.e., a partition, as used herein, formed of dense tissue) of the pericardium along the back of the superior vena cava, and by a pericardial reflection between the right inferior pulmonary vein and the inferior vena cava. The two probes nearly touch each other, separated by the pericardial reflections, in substantial encirclement of the pulmonary veins, and magnetic tips and bands are disposed on the probes to aid in aligning the probes on the opposite sides of the pericardial reflections. An ablation probe is laterally flexible and torsionally rigid to assure proper orientation of applied tissue-ablating energy relative to cardiac tissue along the encircling path around the pulmonary veins. In another procedure according to the present invention, a single endoscopic cannula is used to position an ablation probe around the right and left pulmonary veins via right inter-costal thoracotomy and subxiphoid incisions. In still another procedure according to the present invention, a vacuum-assisted cannula is advanced through the endoscopic subxiphoid cannula for temporary vacuum-controlled attachment to the epicardial surface of the heart.

In accordance with another embodiment of the present invention, the endoscopic cannula is used to enter the pericardium from the subxiphoid approach to attach epicardial tacks and to tension the epicardium between tacks around the annulus of the mitral valve. Specifically, two or more tacks are placed on the epicardial surface near the mitral annulus. The tacks are connected by a suture or wire that may be tensioned to alter the shape and size of the annulus. The tacks may be placed immediately inferior to the left circumflex artery, in the area corresponding to the anterior aspect of the mitral annulus, and immediately inferior to the coronary sinus, in the area corresponding to the posterior aspect of the mitral annulus. The tacks may be helical or spiral titanium tacks of a type, for example, similar to tacks used to fixate prosthetic mesh in laparoscopic hernia repair. Two or more tacks may be inserted into the myocardium, and a suture or wire strand may be threaded through the portion of the tacks that is not embedded into the myocardium. The suture or wire contains loops spaced at varying distances for looping onto the tacks to adjust the amount of tension between the tacks. Tensioning the epicardium in this manner decreases the size of the mitral annulus and corrects the regurgitation due to annular dilation.

BRIEF DESCRIPTION OF THE DRAWINGS

FIGS. 2a-d are, respectively, partial plan, end and sectional views of an endoscopic probe in accordance with one embodiment of the present invention;

FIGS. 4a-c are, respectively, side, bottom and end views of an ablation probe in accordance with one embodiment of the present invention;

FIG. 5 is a plan view of an ablation cannula or probe in accordance with another embodiment of the present invention;

FIGS. 8a, 8b comprise a flow chart illustrating another surgical procedure according to the present invention;

FIG. 9 is a pictorial illustration of an ablation probe and sheath according to one embodiment of the present invention;

FIG. 19 is a partial anterior view of the heart showing the placement in the epicardium of the anterior tack in accordance with the present invention;

FIGS. 20a and 20b are pictorial illustrations of a knotted suture and apparatus for positioning and tensioning the suture between epicardial tacks in accordance with the present invention;

DETAILED DESCRIPTION OF THE INVENTION

Figure 1:
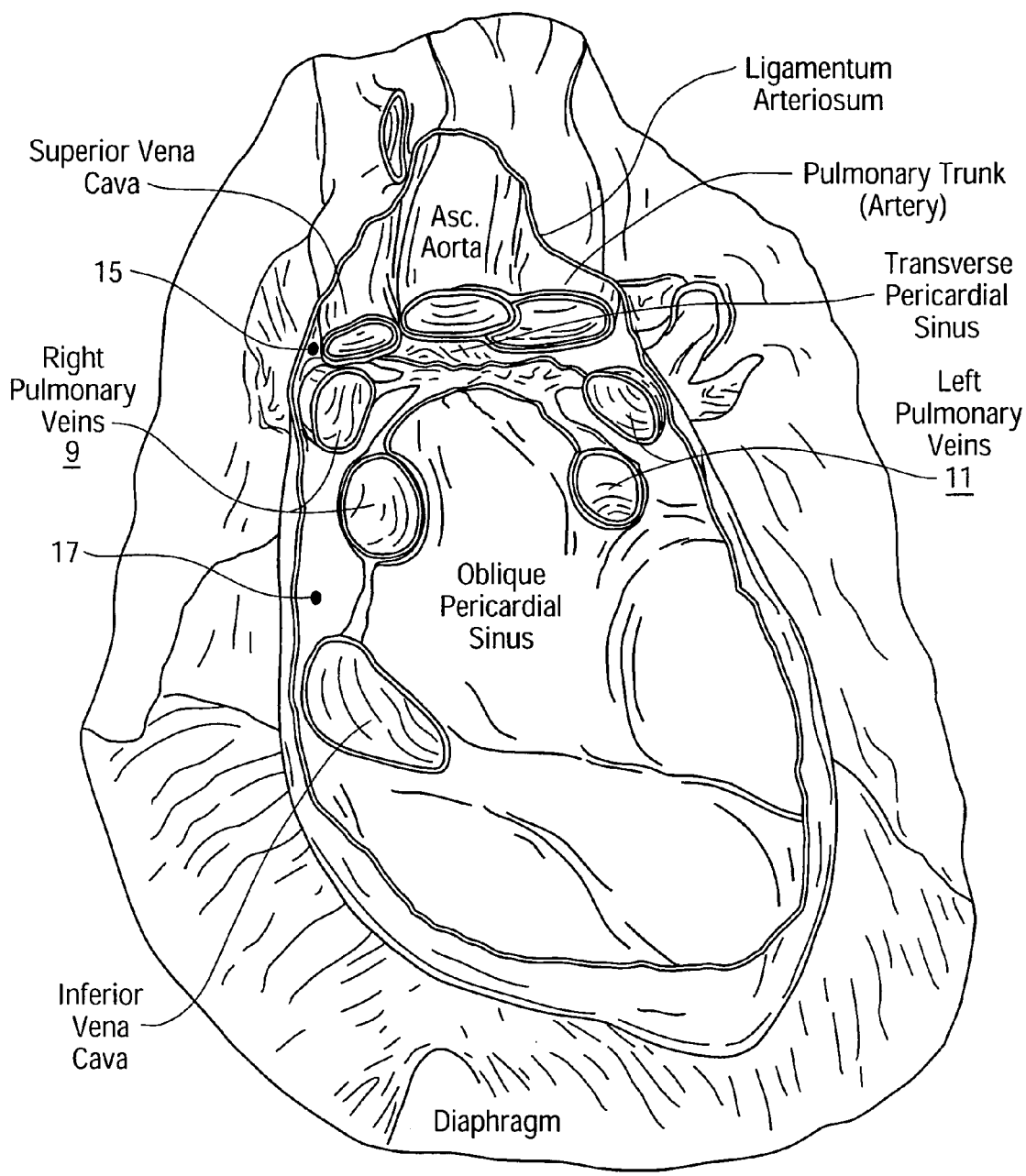
FIG. 1 is a pictorial illustration of the interior of the pericardial sac (anterior view, heart removed)
Figure 3:
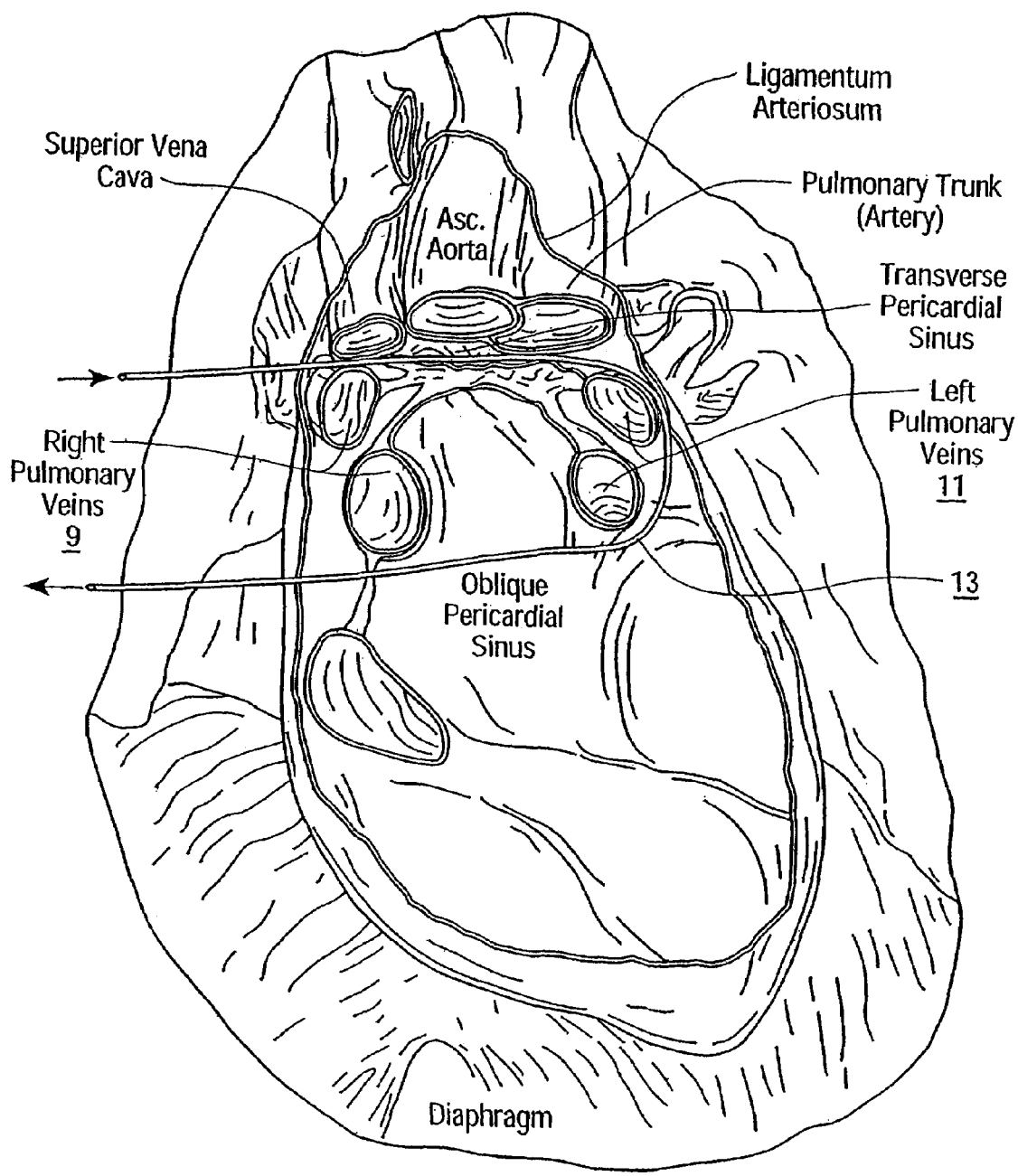
FIG. 3 is a pictorial illustration of the path of an ablation cannula or probe within the intrapericardial space in the illustration of FIG. 1.

Referring now to FIG. 1, there is shown an anterior view of the interior of the pericardial sac (with the heart removed) that indicates the spatial orientations of various vessels including the right and left pulmonary veins 9, 11. A treatment for chronic atrial fibrillation includes ablating cardiac tissue encircling the pulmonary veins 9, 11. This treatment may be accomplished in accordance with the present invention using an endoscopic cannula or probe via subxiphoid and thoracotomy access. Specifically, an ablation probe, as later described herein, or a tubular sheath therefor may be initially threaded around the pulmonary veins along a path 13 as indicated in FIG. 3, and the ablation probe may be subsequently advanced into position along the path 13 through the tubular sheath. In one embodiment, an endoscopic cannula enters the pericardium from a subxiphoid incision along a dissected channel in order to visualize the superior vena cava and place an illuminating clip, as later described herein, at a location 15 on the pericardium adjacent the superior vena cava. Of course, other detectable energy sources or elements may also be positioned in an end effector such as a scissor-like structure including blades or jaws or other effector elements, or in a distal-end illuminator in place of an illuminated chip, using detectable sources such as infrared, ultrasound, fluoroscopy, and the like. The endoscopic cannula is then also used to visualize the inferior vena cava and an illuminated clip or other detectable energy source is then also attached to the pericardium at a location 17 adjacent the inferior vena cava. Once in a desired position, the jaws of the clip 27 are closed on pericardial tissue, for example, by sliding the shaft 23 and manual manipulator 25 backward relative to the tubular body 21. The dimensions of the illuminated clip 27, including the tubular body 21 and the manipulator 25, are smaller than the cross sectional dimensions of the instrument channel of the subxiphoid endoscopic cannula, which can therefore be removed from the body while leaving the illuminated clip in place. Similarly, if a fiber optic cable is attached to the clip, the smaller dimensions of the fiber optic cable and clip allow removal of subxiphoid endoscopic cannula while leaving the clip in place to be illuminated by subsequent attachment of a light source to the proximal end of the fiber optic cable. The endocopic cannula can then be removed from the mediastinum following attachment of the clip for insertion of the endoscopic cannula (or insertion by another endoscopic cannula) into the right pleural cavity through a small thoracotomy incision. The light from each clip, or other detectable energy source, as discussed above, at the locations 15, 17 aids in guiding a pericardial entry instrument, and in guiding an endoscopic cannula with a transparent tapered tip during blunt tissue dissection under the superior and inferior vena cava along the path 13, 19 within the intrapericardial space, as shown in FIG. 3.

Referring now to the views in FIGS. 2a-d of an illuminated clip, there is shown an elongated tubular body 21 which can be rigid or flexible or malleable or otherwise adjustable, articulateable or steerable. The tubular body 21 includes an inner lumen extending therethrough between distal and proximal ends thereof. An inner shaft 23, which can have the physical characteristics described above for body 21, is slidable within the lumen in the tubular body 21, and includes a manual manipulator 25 attached to the proximal end and a clip 27 with resilient jaws or other suitable attachment mechanism such as barbs disposed in attached or detachable configuration to the distal end of the shaft 23. A square, or other non-rotational shape of the tubular body 21, as shown in the sectional view of FIG. 2b, retains a mating shape of clip 27 in proper alignments with slots 29 that are oriented to facilitate expansion of the jaws of clip 27 toward an open configuration. As the shaft 23 and manual manipulator 25 and clip 27 slide forward relative to tubular body 21, the jaws of the clip resiliently extend into the open configuration, as shown. One or more of the jaws of clip 27 may include a light-emitting diode (LED) 26 as a light source for transluminating the surgical site through the pericardium to which the jaws may attach. Of course, other light sources such as point-to-point cabling of optical fibers from a remote light source to the jaws of clip 27 may also be used, and a switch 24 or other controller may be housed in the manual manipulator 25 for convenient control of light made selectively available at the clip 27 that is positioned, for example, in the manner as previously described.

Figure 17:
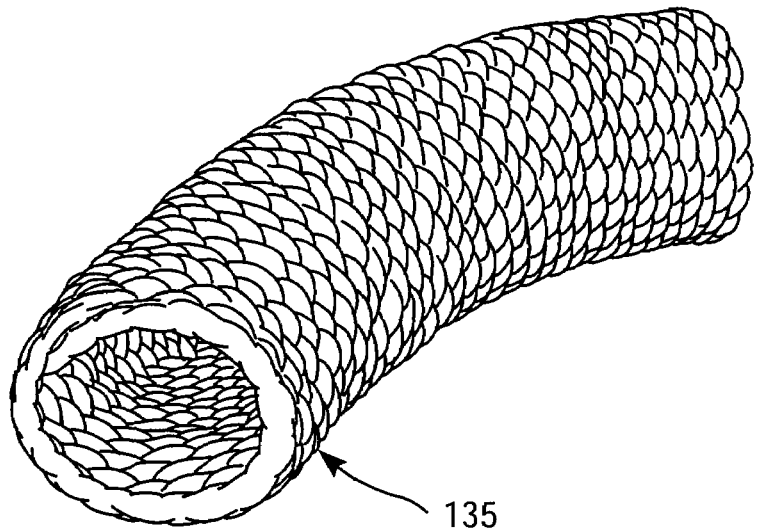
FIG. 17 is a pictorial view of a braided sheath that promotes torsional rigidity for properly orienting an ablation probe.

Referring now to FIGS. 4a-c, there is shown an embodiment of a tissue-ablating instrument or probe according to one embodiment of the present invention that can be inserted in the dissected channel through tissue (or in the insertion tube therefor) along the path 13, 19 within the intrapericardial space. Specifically, the tissue-ablating instrument includes a flexible or steerable or articulatable guide or sheath 31 and an articulated backbone 33 attached to the sheath 31 along a selected length of the instrument. In one embodiment, the backbone 33 includes a plurality of successive segments 33 that are each pinned 32 or hinged together in iterative tongue 34 and groove 30 array, as illustrated in FIGS. 4a, 4b, 4c, to provide lateral flexibility with torsional and longitudinal rigidity. Alternatively, a braided sheath 135, as illustrated in FIG. 17, may include non-round cross section to facilitate retaining an ablation probe of similar non-round mating shape in proper axially angular orientation during slidable positioning along the length of the sheath. In other embodiments, the backbone may provide telescoping control of length and/or torsional control in conventional manner to facilitate twisting all or part of the length thereof into conformal orientation against cardiac tissue. Also, these forms of control over the mechanical characteristics of the supporing backbone facilitate the manipulation of the ablating instrument through the anatomy. This assures that the ablating instrument can be positioned and retained in continuous orientation toward or against cardiac tissue along the path 13, 19 anterior to the posterior pericardium for proper application of tissue-ablating energy only to the cardiac tissue. For example, the distal portions of the ablation probes contain a section that emits tissue-ablating energy. The supplied energy at various wavelengths heats cardiac tissue. Radio-frequency energy may be monopolar, that is, the current supplied via the probe travels through the patient's body to a cutaneous grounding pad. A radio-frequency probe may also be bipolar; that is, current travels between two spaced conductor bands on the probe. There may be multiple spaced bands disposed on the probe to promote current conduction between adjacent bands. Microwave energy may be emitted from a microwave antenna placed in the distal probe. The emitted microwave energy may heat tissue in proximity to the antenna, in contrast to radio frequency probes which must make contact with tissue to cause heating. Ultrasound probes incorporate a transducer in the probe that converts electrical signals into ultrasonic energy that vibrates cells in tissue to generate heat. Probes may contain fiberoptic cables to carry laser light to tissue for heating. Light in the infrared region may also be transmitted through fiberoptics to heat cardiac tissue. A flexible sheath 31 attached to the backbone 33 may house a conduit for tissue ablating-energy, and the sheath may be relatively movable with respect to the backbone along a captivating track, as illustrated in FIG. 4c, for enhanced ability to manipulate the ablating instrument into proper position. The tissue-ablating energy may then be supplied via a distributed electrical heater element, or a distributed electrode for RF electrical energy, or an infrared conduit, or a microwave instrument in conventional manner (see, for example, U.S. Pat. No. 6,383,182).

In the configuration of the instrument, as illustrated in FIGS. 4a-c, the sheath 33 containing one or other such tissue-ablating mechanisms may be positioned as previously described and oriented toward cardiac tissue within the intrapericardial space along the entire path 13, 19. The active, tissue-ablating segment need not be longer than approximately the distance along the portion of the path 13, 19 of insertion around the set of four pulmonary veins. Alternatively, the tissue-ablating segment of the instrument may be substantially shorter than the path 13, 19 around the pulmonary veins and may be applied serially along the path 13, 19 to ablate tissue along the entire path. Following application of tissue-ablating energy along the path 13, 19, the tissue-ablating instrument may be withdrawn from the patient's body.

Figure 6:
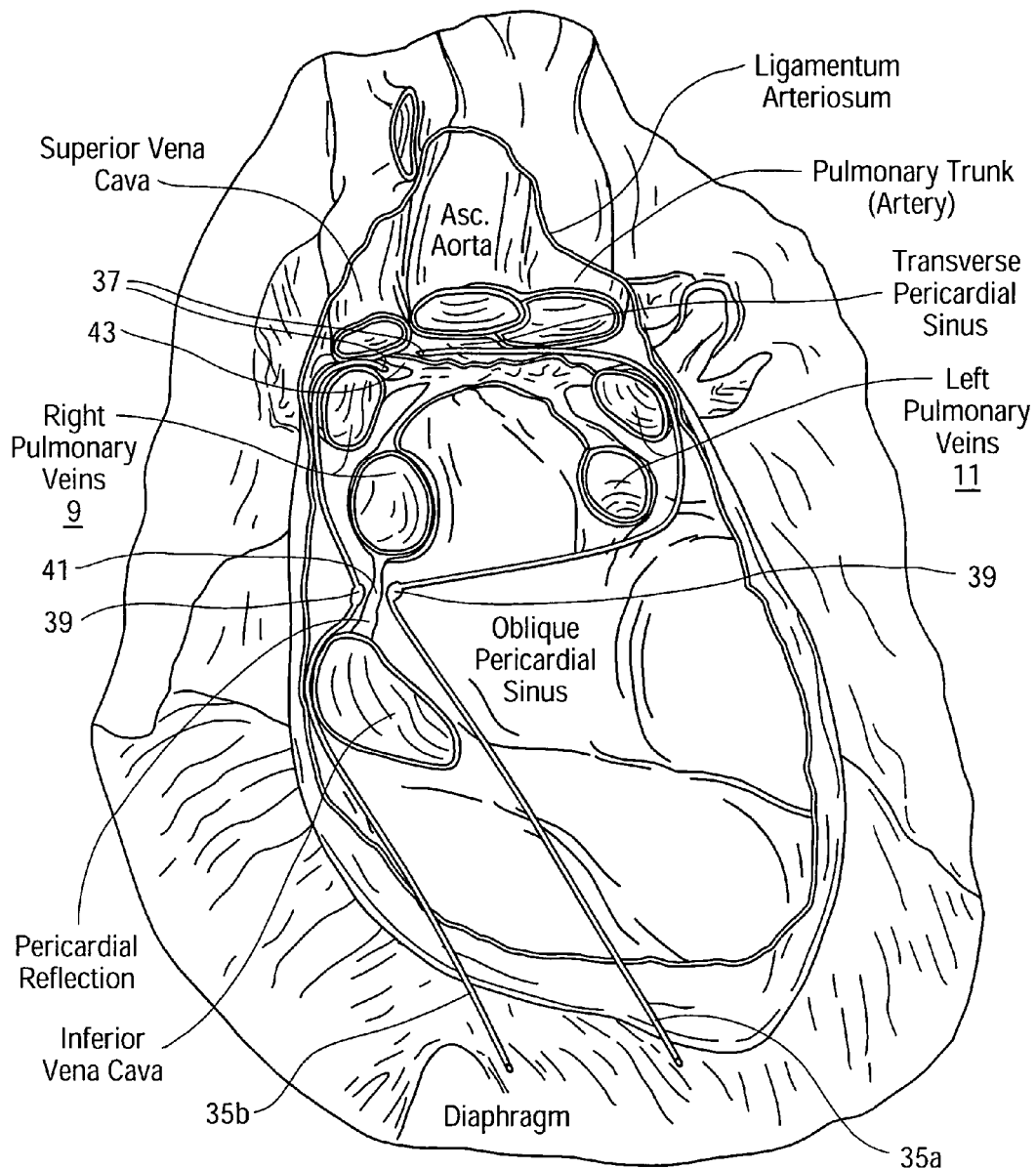
FIG. 6 is a pictorial illustration of the path of ablation cannulas or probes within the intrapericardial space in the illustration of FIG. 1 achieved with probes of the embodiment illustrated in FIG. 5.

Referring now to FIG. 5, there is shown another embodiment of a tissue-ablating probe in accordance with the present invention in which a flexible elongated body 35, for example, as illustrated and described above with reference to FIGS. 4a-c, also includes magnetic components 37, 39 at the distal end and at a location proximal the distal end for selectively positioning a pair of such tissue-ablating probes along paths, as shown in FIG. 6. Portions of the ablation probes 35 proximal the magnetic bands 39 may include electrically insulating sheaths 40, for example, to limit exposure of cardiac tissue to RF energy only along the portions of the probes 35 intermediate the tips 37 and bands 39. It is desirable to conduct the tissue-ablating procedure from the subxiphoid access site to avoid multiple incisions in a patient's chest, either as thoracotomy incisions or thoracoscopic incisions.

Therefore, to encircle the pulmonary veins within the intrapericardial space, as shown in FIG. 6, two tissue-ablating probes 35a, 35b may be advanced along the posterior pericardial surface within the intrapericardial space. One probe 35a may be advanced along the left lateral aspect of the pericardium, track superior to the left superior pulmonary vein, and enter the transverse pericardial sinus. The transverse sinus ends near the right superior pulmonary vein. Inferiorly, the probe 35a may track inferior to the left inferior pulmonary vein, transversely across the oblique pericardial sinus toward the right inferior pulmonary vein, where the probe encounters a pericardial reflection 41 extending between the right inferior pulmonary vein and the inferior vena cava. The second probe 35b is advanced along the right lateral aspect of the pericardium, tracking lateral to the inferior vena cava, right inferior pulmonary vein, and right superior pulmonary vein. The probe 35b tracks superior to the right superior pulmonary vein, until its tip rests close to the tip of the probe 35a in the transverse sinus. A reflection 43 of the pericardium lies along the back of the superior vena cava, and this fold of pericardium separates the tips 37 of the two probes 35a, 35b.

In order to form a substantially continuous ring of ablated tissue surrounding the pulmonary veins, it is desirable to have the tips 37 of the probes 35a, 35b nearly touch each other, although they are separated by a pericardial reflection 43. The distal tips 37 of the probes 35a, 35b contain magnets of opposite polarity to cause the probes to align themselves via magnetic attraction on opposite sides of the pericardial reflection 43 that separates the tips 37. Additionally, the magnetic bands 39 on the ablating probes 35a, 35b substantially align through the pericardial reflection 41 due to the attractive magnetic forces involved. The magnetic bands 39 may be adjusted along the lengths of the probes 35a, 35b to accommodate the patient's anatomy in positioning the magnets properly in close proximity.

The probes 35a, 35b may be formed with resilience and a predetermined bend, and be retained in straightened-out configuration by a rigid outer sheath that facilitates positioning the probe around corners and into the transverse sinus. For example, the probe 35a may have a preformed ninety-degree bend several centimeters proximal to its distal tip. The probe is inserted through a straight, rigid cannula, and advanced through the operating channel of the endoscopic subxiphoid cannula. The probe 35a is positioned superior to the left superior pulmonary vein, and the cannula retracted to allow the probe to bend and enter the transverse sinus. The probe 35a is advanced further and fully into the transverse sinus. Alternatively, the probe 35a may have an inner lumen that accepts a bent stylet which is inserted into the probe whenever a bend in the probe is desired. A relatively rigid, straight outer sheath may also be used in combination with an inner bent stylet. Specifically, as the bent stylet, which is initially retracted out of the probe 35a, is advanced distally into the probe 35a, the portion of the probe 35a that lies distal to the rigid, straight outer sheath will take the shape of the bent stylet.

The ablation probe 35a, 35b is flexible. A variety of energy sources may achieve ablation of cardiac tissue; e.g. radio frequency, microwave, ultrasound, laser radiation, infrared illumination, and the like. For example, the distal portions of the ablation probes contain a section that emits tissue-ablating energy. The supplied energy at various wavelengths heats cardiac tissue. Radio-frequency energy may be monopolar, that is, the current supplied via the probe travels through the patient's body to a cutaneous grounding pad. A radio-frequency probe may also be bipolar; that is, current travels between two spaced apart conductor bands on the probe. There may be multiple spaced bands disposed on the probe to promote current conduction between adjacent bands. Microwave energy may be emitted from a microwave antenna placed in the distal probe. The emitted microwave energy may heat tissue in proximity to the antenna, in contrast to radio frequency probes which must make contact with tissue to cause heating. Ultrasound probes incorporate a transducer in the probe that converts electrical signals into ultrasonic energy that vibrates cells in tissue to generate heat. Probes may contain fiberoptic cables to carry laser light to tissue for heating. Light in the infrared region or from a high-energy laser may also be transmitted through fiberoptics to heat cardiac tissue. The ablation probe is flexible and may have various controllable mechanical characteristics, for example, as previously described herein with reference to FIGS. 4a-c. In another embodiment, as illustrated and later described herein with reference to FIG. 17, a braided structure forms the length of the probe body 35. A magnetic band 39 is selectively located at axial positions along the probe as desired, for example, by using a pair of endoscopic graspers inserted through an instrument channel in the subxiphoid endoscopic cannula to slide the band 39 along the probe to a selected position, as shown in FIG. 5. The magnetic band 39 on each probe 35a, 35b may be moved in this manner to positions aligned with the common site directly under the right inferior pulmonary vein to magnetically draw the probes together across the pericardial reflection between the right inferior pulmonary vein and the inferior vena cava, as shown in FIG. 6. Helical tacks or barbs can be located at the tips 37 of the probes to temporarily anchor the probes at the location 43 adjacent the pericardial reflection.

In the treatment of chronic atrial fibrillation, it is desirable to ablate the atrial tissue surrounding the four pulmonary veins (i.e., the left and right superior and inferior pulmonary veins). An ablation probe may be used to ablate the atrial tissue surrounding all four pulmonary veins in a single circle. Alternatively, the two left pulmonary veins and the two right pulmonary veins may be encircled separately in ablation rings.

Figure 7A:
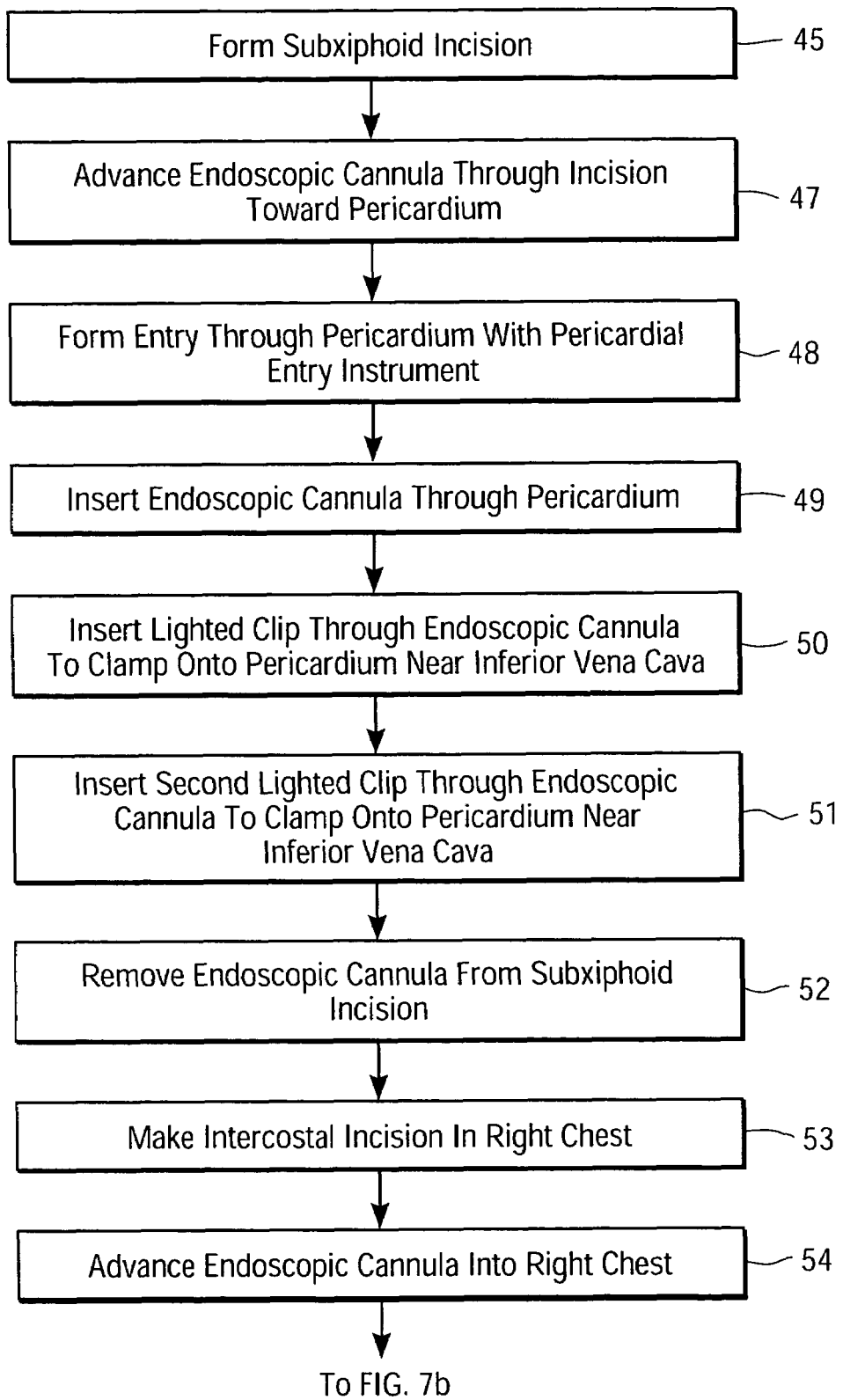
FIGS. 7a and 7b comprise a flow chart illustrating one surgical procedure according to the present invention.
Figure 7B:
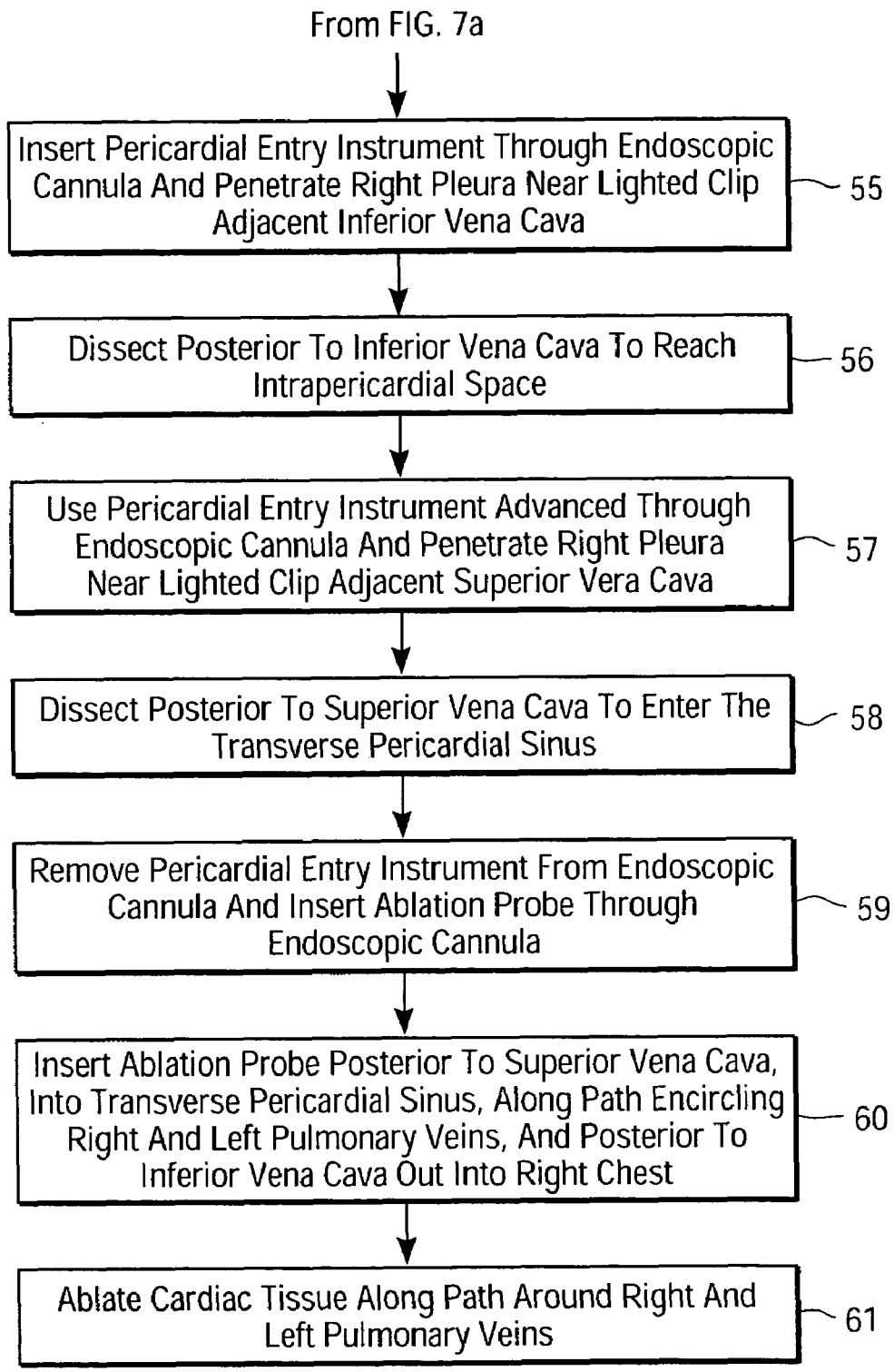

In accordance with one embodiment of the present invention, an ablation probe is placed endoscopically, as illustrated in the flow chart of FIGS. 7a and 7b. Specifically, using an endoscopic cardiac access cannula, inserted through a subxiphoid incision, the anterior pericardium is identified and entered. The endoscopic cannula is advanced to the lateral border of the superior vena cava within the pericardium. A small, 2 cm incision is made in the right chest, at approximately the 5$^{th}$ intercostal space and the anterior axillary line. A second endoscopic cannula is advanced into the right pleural cavity to dissect the tracts posterior to the superior and inferior vena cavae. A light source supplying the endoscopic cannula in the right pleural cavity may be dimmed or extinguished to allow light from the subxiphoid endoscopic cannula to transilluminate through the pericardial and pleural layers to mark the correct spot for vena caval dissection. The pericardial entry instrument may be used to grasp and enter through the pleural and pericardial layers. Following dissection of a tract posterior to the superior vena cava, the ablation probe may be advanced from the right pleural cavity through the dissected tract into the transverse pericardial sinus and lateral to the left pulmonary veins. A grasping instrument may be advanced through the subxiphoid endoscopic cannula to grasp the probe and pull it into position around the pulmonary veins. The subxiphoid endoscopic cannula is then advanced to the lateral border of the inferior vena cava, and the endoscopic cannula in the right pleural cavity is used to dissect a tract posterior to the inferior vena cava, using the transilluminated light from the subxiphoid endoscopic cannula to pinpoint the location of the dissection tract. Following dissection of the tract posterior to the inferior vena cava, the pericardial entry instrument used for the dissection may grasp the distal end of the ablation probe and pull it out through the dissected tract to complete enrichment of all four pulmonary veins.

The ablation probe remains in the same axial orientation along its length. Torsional deflection of a portion of the probe may lead to ablation of unintended tissue adjacent the left atrium; for example the esophagus. Application of ablation energy to the esophagus may cause perforation and/or necrosis of the esophagus, with subsequent leakage, scarring and stricture. If a flexible ablation probe is used for the procedure, prior insertion of a non-torsional sleeve posterior to the vena cavae and around the pulmonary veins may prevent twisting of the ablation lead. A tubular sleeve 135, as illustrated in FIG. 17, may contain a braided support in its wall that maintains axial alignment of the sleeve along its flexible length. The tubular sleeve 135 contains an off-round cross-section, (e.g., elliptical or substantially rectangular) and the flexible ablation probe has a matching cross-section to prevent the probe from twisting out of axial alignment as it is advanced through the length of the non-torsional tubular sleeve 135. Manipulation with the endoscopic instruments of the separate sleeve 135 through the dissected tracts and around the pulmonary veins is desirable to prevent injury to the ablation probe from the pulling and grasping movements exerted during encirclement of the pulmonary veins. The braided support in the tubular sleeve 135 may be constructed of plastic material (e.g., nylon, polyethylene) to allow transmission of ablation energy through the wall of the tubular sleeve without significant absorption of the energy. If the ablation probe uses a microwave or ultrasonic source, the energy may be transmitted through the tubular sleeve into the myocardium of the heart.

More specifically, the flow chart of FIGS. 7a and 7b illustrates a surgical procedure in accordance with one embodiment of the present invention. A subxiphoid incision is formed 45, and an endoscopic cannula is advanced 47 through the incision and mediastinum toward the pericardium. A pericardial entry instrument is inserted through the endoscopic cannula to form an entry 48 through the pericardium. The endoscopic cannula is inserted through the entry in the pericardium 49. An illumination source is inserted through the endoscopic cannula to attach 50 to the pericardium near the superior vena cava. A second illumination is inserted 51 through the endoscopic cannula to clamp to the pericardium near the inferior vena cava. The endoscopic cannula is removed 52 from the subxiphoid incision. An intercostal incision is made 53 in the right chest. The endoscopic cannula is advanced 54 through the incision into the right chest cavity. The pericardial entry instrument is inserted through the endoscopic cannula and used to penetrate the right pleural 55 near the illumination source adjacent the inferior vena cava. Dissection 56 is conducted posterior to the inferior vena cava to reach the intrapericardial space. The pericardial entry instrument is used through the endoscopic cannula to penetrate the right pleural 57 near the illumination source adjacent the superior vena cava. Dissection 58 is conducted posterior to the superior vena cava to reach the tranverse pericardial sinus. The pericardial entry instrument is removed 59 from the endoscopic cannula and the ablation probe is inserted 60 through the endoscopic cannula. The ablation probe is inserted posterior to the superior vena cava into the intrapericardial space in the transverse pericardial sinus, along a path encircling the right and left pulmonary veins, and posterior to the inferior vena cava out into the right chest. The cardiac tissue is ablated 61 along a path around the right and left pulmonary veins to form a transmural lesion along the path.

Figure 8A:
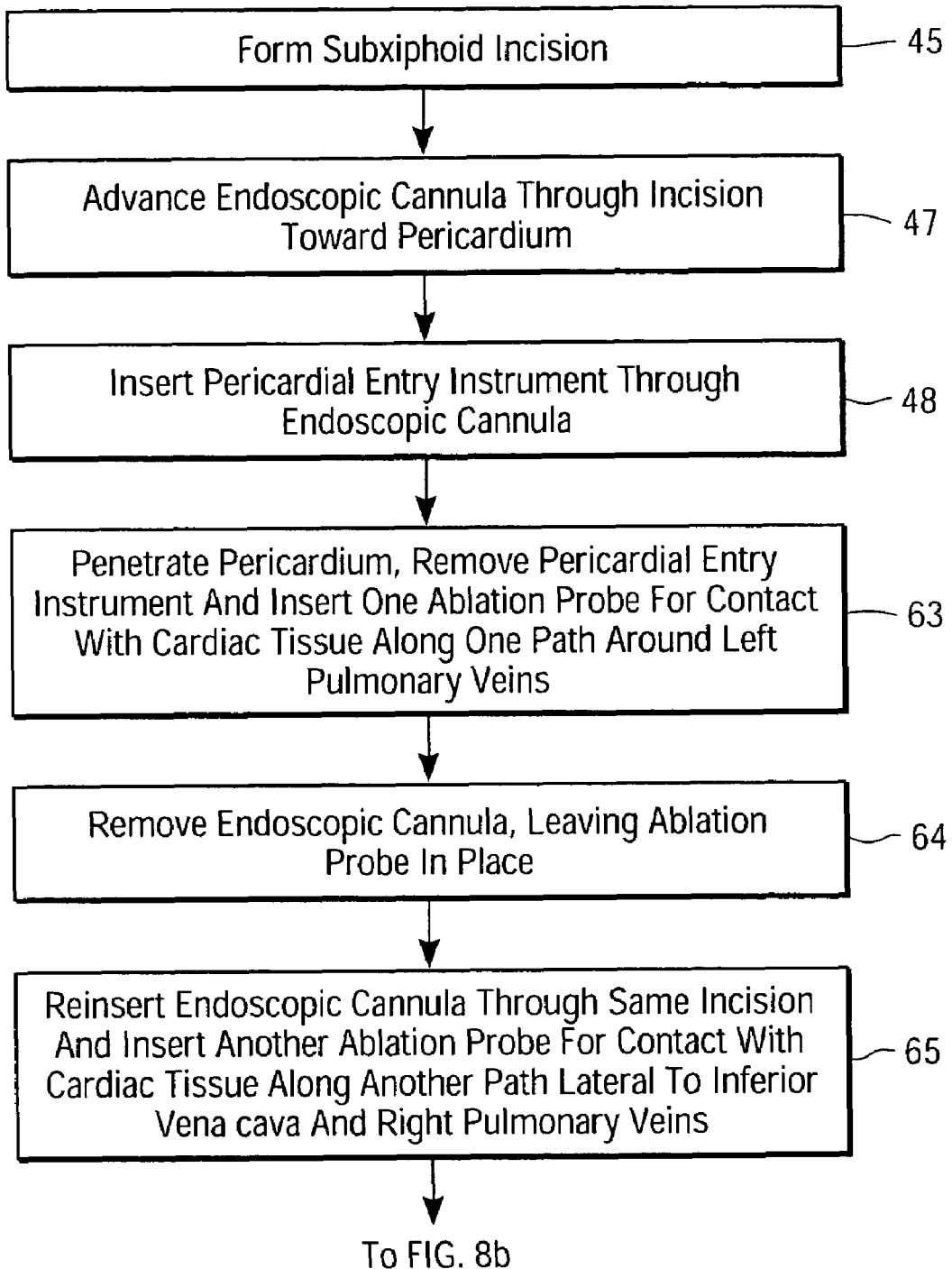

Referring now to FIGS. 8a, 8b, there is shown a flow chart illustrating another surgical procedure in accordance with an embodiment of the present invention. The procedure includes forming a subxiphoid incision 45 and advancing a subxiphoid endoscopic cannula through the incision toward the pericardium 47, in a manner as previously described. A pericardial entry instrument is inserted 48 through a subxiphoid endoscopic cannula and advanced into contact with the pericardium at a location near its anterior apical region. The pericardium is then penetrated, entered with the subxiphoid endoscopic cannula, and the entry instrument is removed from the body. An ablation probe is inserted 63 through the endoscopic cannula and into the intrapericardial space along one path around the left pulmonary veins and laterally along the transverse pericardial sinus. The probe is advanced lateral to the left inferior and left superior pulmonary veins. The opening to the transverse pericardial sinus is visualized superior to the left superior pulmonary vein, through the endoscopic cannula. The probe is advanced into the opening to the transverse pericardial sinus, and is pushed further to the end of the sinus. The tip of this ablation probe extends to the pericardial reflection adjacent the superior vena cava, corresponding to the end of the transverse pericardial sinus. The endoscopic cannula is then removed 64 leaving the probe in the transverse pericardial sinus. The endoscopic cannula is then reinserted through the same subxiphoid incision and same pericardial opening for insertion therethrough of another ablation probe 65 along another path lateral to the inferior vena cava.

The tips of these ablation probes substantially align 67 on opposite sides of the pericardial reflection adjacent the superior vena cava as a result of magnetic attraction between oppositely-poled magnetic tips. In addition, the one and other ablation probes are manipulated into close proximity 69 along their lengths on opposite sides of the pericardial reflection between the right inferior pulmonary vein and the inferior vena cava. Magnetic bands on each of the ablation probes are located at positions along the respective lengths of the ablation probes to magnetically attract into substantial alignment 70 on opposite sides of the pericardial reflection between the right pulmonary vein and the inferior vena cava. With the associated tips and bands of the ablation probes aligned in close proximity, the ablation probes are then activated 71 to apply tissue-ablating energy to cardiac tissue along the substantially continuous encircling path thus formed by the two ablation probes.

Figure 10:
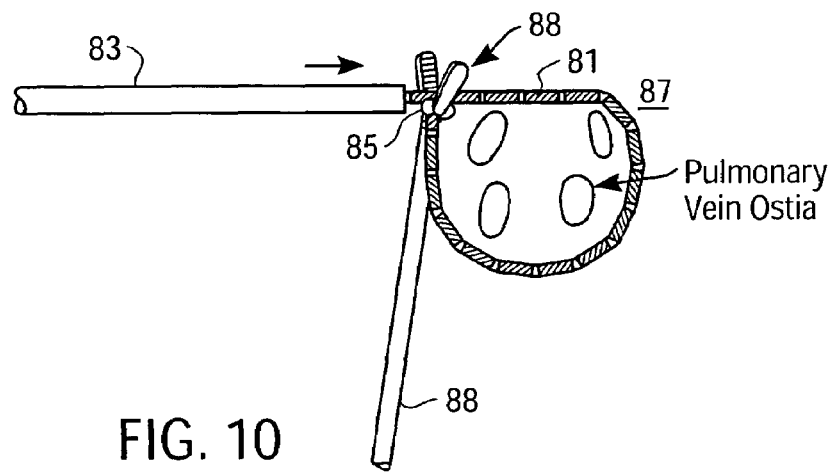
FIG. 10 is a pictorial illustration of a configuration of the probe according to FIG. 9 following a surgical procedure according to the present invention.
Figure 13:
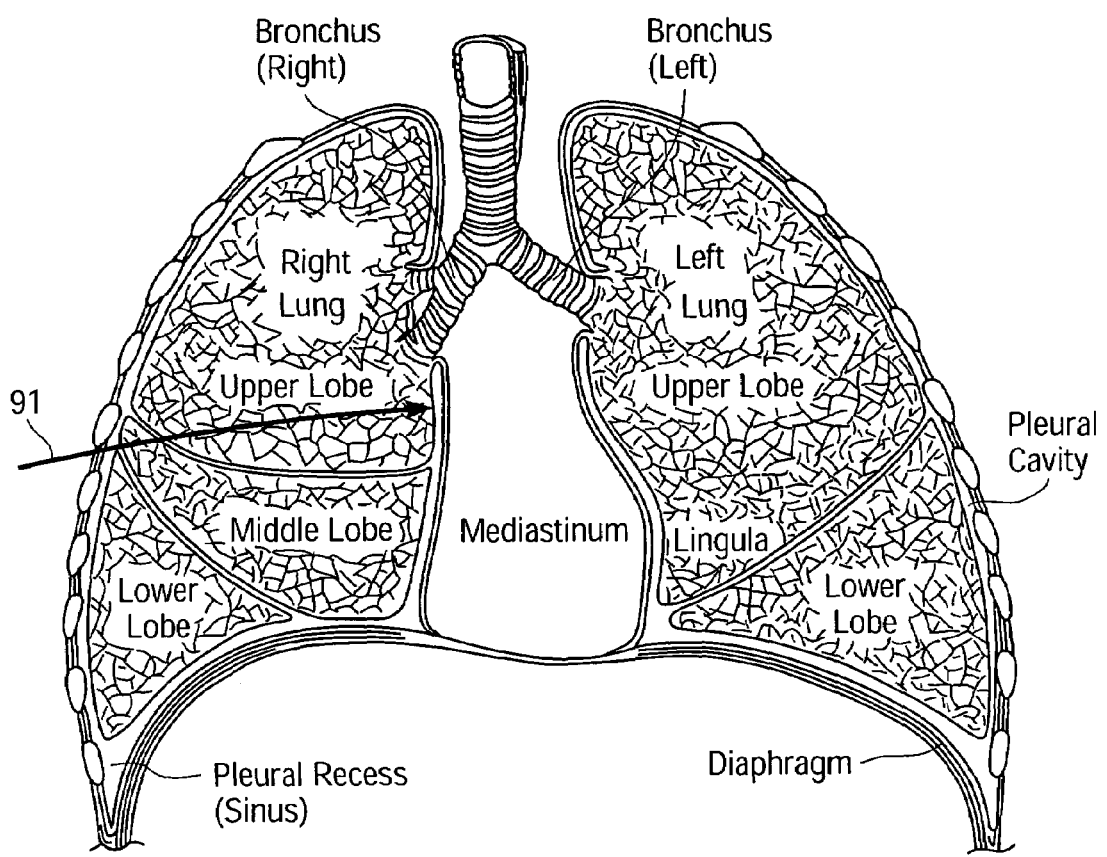
FIG. 13 is a partial anatomical illustration of a surgical procedure according to the present invention.
Figure 11A:
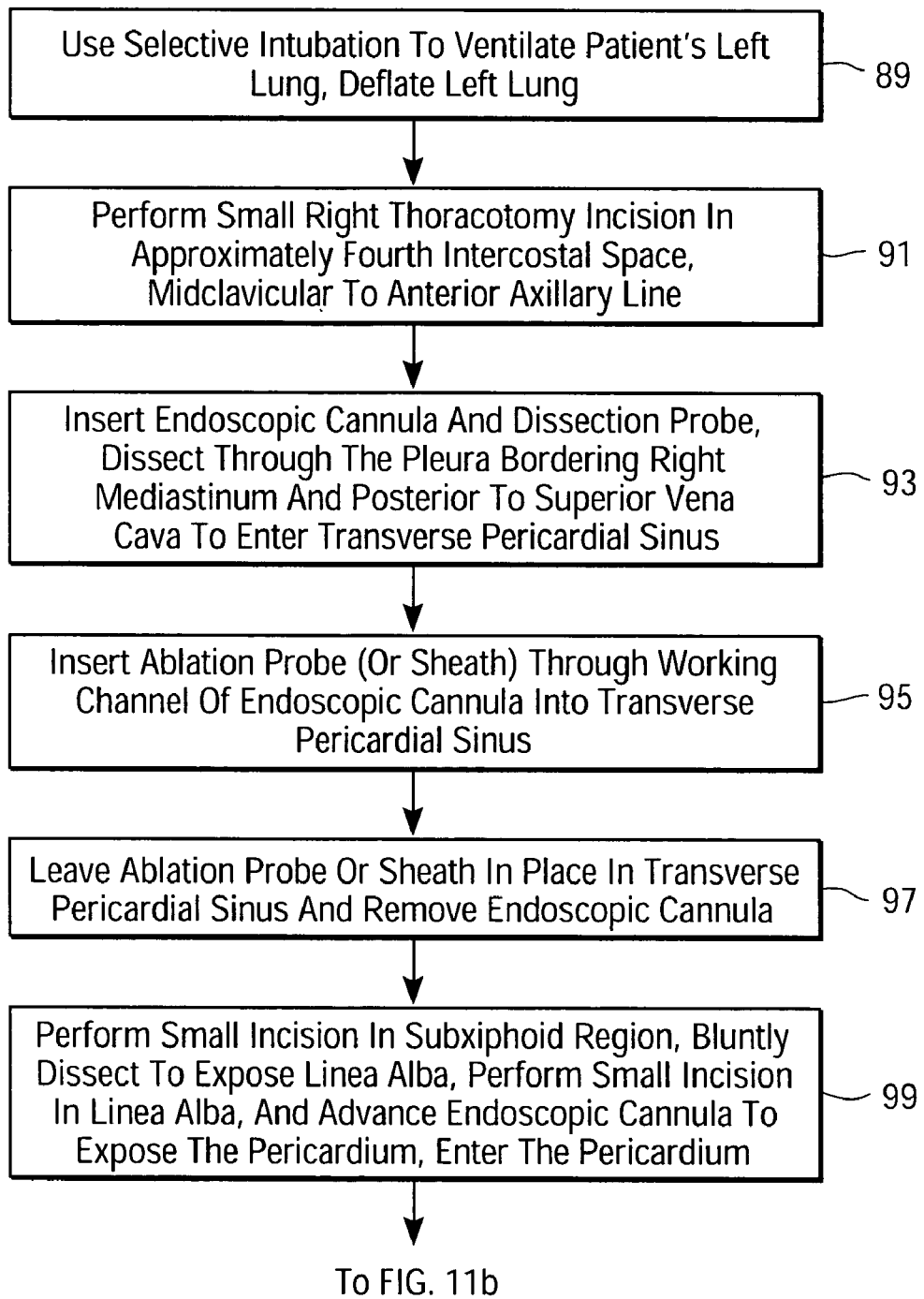
FIGS. 11a, 11b comprise a flow chart illustrating a surgical procedure according to one embodiment of the present invention.
Figure 11B:
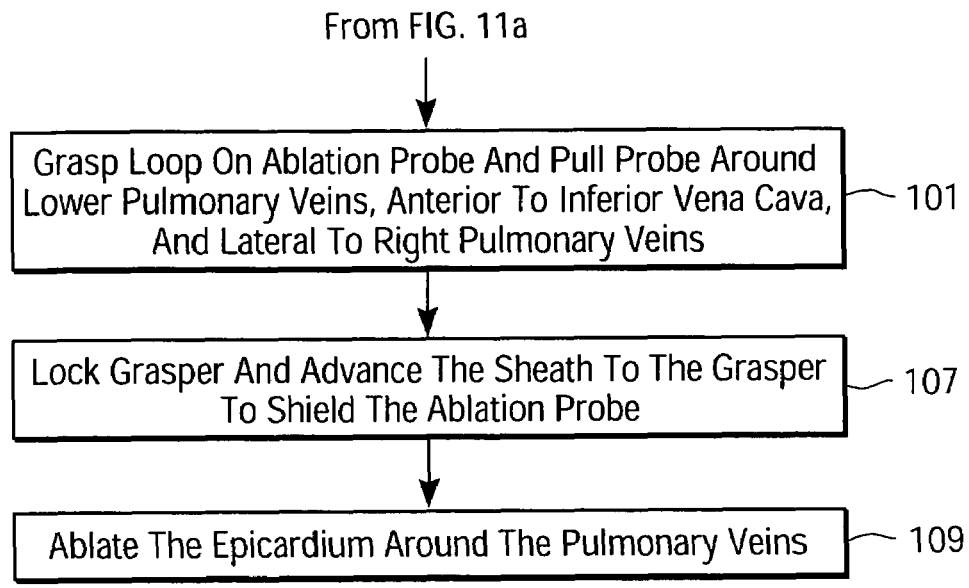
Figure 12:
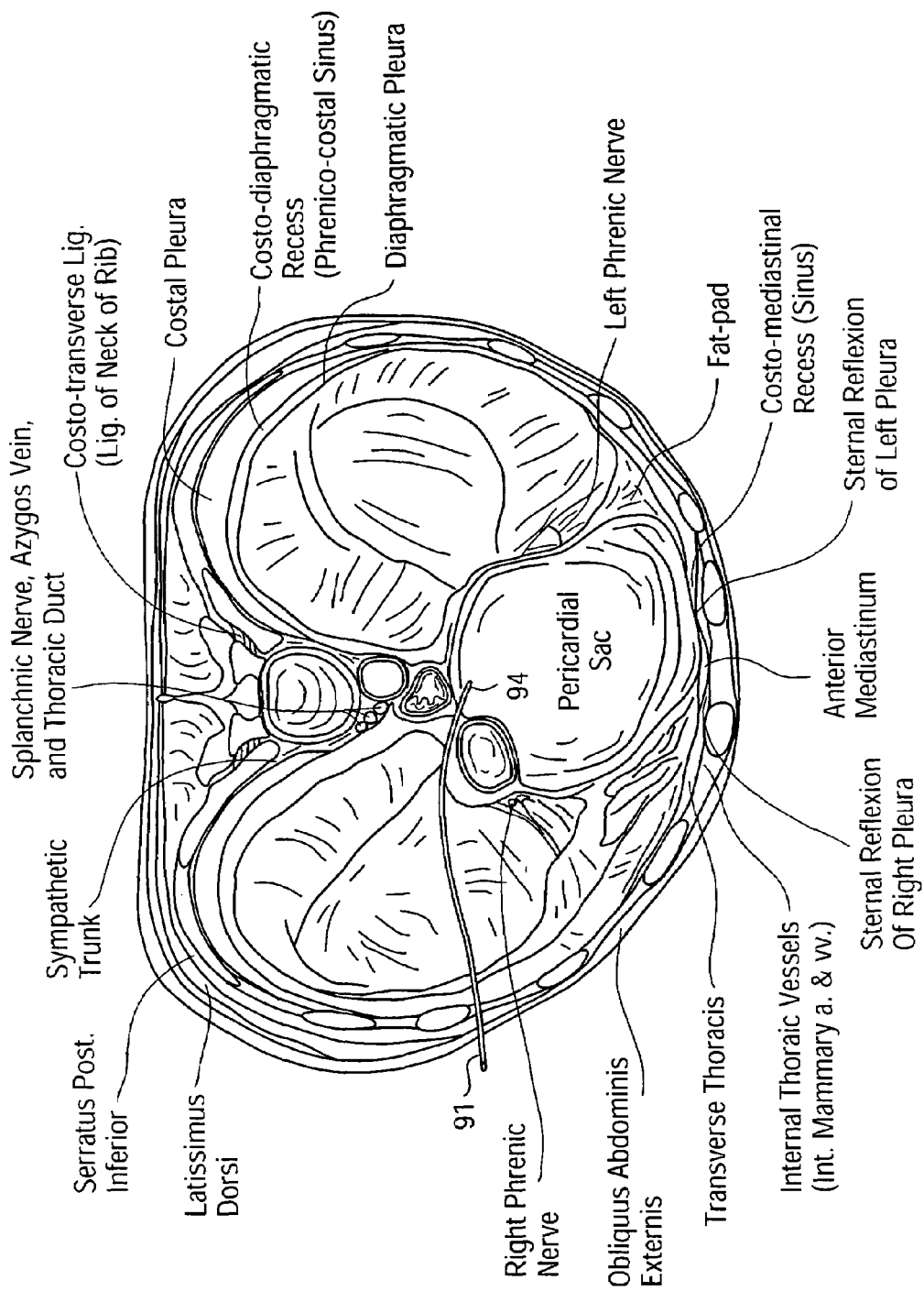
FIG. 12 is a top anatomical sectional view illustrating a surgical procedure according to the present invention.

Referring now to FIG. 9, there is shown an ablation probe 81 that is slidable within an insertion sheath 83, and that is laterally flexible at least in one direction but that is torsionally and longitudinally rigid, for example, attributable to a backing structure of tongue and groove segments that are successively pinned or hinged together, as illustrated and described herein with reference to FIGS. 4a, 4b. In this embodiment, the ablation probe 81 includes a suture loop 85 attached at the distal end of the probe 81 to facilitate gripping and pulling of the probe for placement along a path 87 substantially encircling the pulmonary vein ostia, as illustrated in FIG. 10. To position the ablation probe 81 within the intrapericardial space encircling the pulmonary vein ostia, a surgical procedure is performed as illustrated in the flow chart of FIGS. 11a, 11b. Initially, the patient is prepared for surgery and selective intubation is installed to ventilate the patient's left lung 89. The patient's right lung is deflated and a small right thoracotomy incision is performed 91 on the fourth intercostal space approximately mid-clavicular to the anterior axillary line, as shown on FIGS. 12 and 13. An endoscopic cannula equipped with a tissue-dissecting probe or tip is inserted into the incision to dissect through the pleural 93 bordering the right mediastinum and posterior to the superior vena cava in preparation for entering the transverse pericardial sinus. The ablation probe (or a sheath therefor) is inserted 95 through a working channel in the endoscopic cannula and into the transverse pericardial sinus. A distal end of the ablation probe (or of the sheath therefor) is left in place in the transverse pericardial sinus as the endoscopic cannula is removed 97 back through the dissected channel, leaving the ablation probe (or sheath therefor) in place.

Then, a small incision is formed in the subxiphoid area and tissue is bluntly dissected to expose the linea alba. An incision is made in the linea alba in order to advance 99 the endoscopic cannula posterior to the sternum toward the pericardium. The pericardium is penetrated and a grasping instrument is inserted through the working channel in the endoscopic cannula and into the intra-pericardial space to grasp the loop 85 on the distal tip of the ablation probe 81 and pull the probe laterally around the left pulmonary veins 101 to a level below the left inferior pulmonary vein.

The loop 85 on the tip of the ablation probe 81 is then grasped and pulled across the oblique pericardial sinus toward the right border of the pericardium, anterior to the inferior vena cava, and then upwardly lateral to the right pulmonary veins toward the ablation probe at its entrance into the transverse pericardial sinus. The grasper 88 may now orient the tip 85 of the ablation probe 81 in proximity to the portion of the probe at its entrance into the transverse pericardial sinus in a configuration, as illustrated in FIG. 10. The grasper 88 may be locked to retain the distal end and the entry position of the ablation probe 81 substantially in contact 107 as the sheath 83 of thermally insulating material is advanced over the ablation probe 81 toward the grasper to thermally shield the portion of the ablation probe 81 that extends from the grasper 88 toward the intercostal incision 91. With the ablation probe 81 encircling the left and right pulmonary veins substantially as shown in FIG. 10 and oriented toward cardiac tissue within the intrapericardial space, the ablation probe may then be energized, for example, by application thereto of RF or microwave electrical signal or other tissue-ablating energy, to ablate the epicardium 109 to create a transmural lesion in the endocardium around the pulmonary veins. Thereafter, the grasper 88 is unlocked and the ablation probe 81 is removed from around the pulmonary veins, and the incisions performed during the surgical procedure are sutured.

Figure 14:
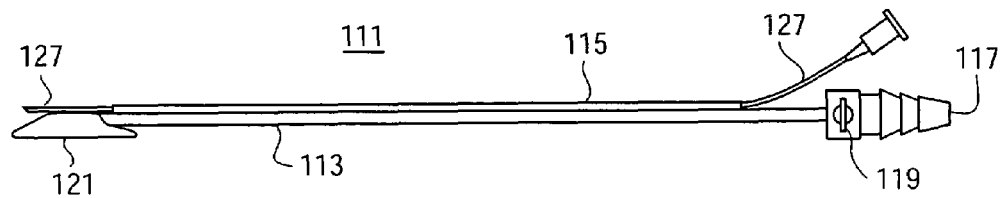
FIG. 14 is a plan view of a suction cannula in accordance with one embodiment of the present invention.

Referring now to FIG. 14, there is shown a plan view of a vacuum-assisted suction cannula 111 including an inferior suction channel 113 and a superior instrument channel 115 aligned therewith substantially over the entire length of the inferior suction channel 113 between distal and proximal ends thereof. The cannula 111 may be flexible, steerable, articulatable, rigid, twistable or have other desirable mechanical characteristics that facilitate manipulation of an ablation probe, as previously described herein. Specifically, the proximal end of the inferior suction channel 113 includes a hose connection 117 for attachment to a vacuum supply, and a manually-controllable suction valve 119 for selectively altering the pressure differential relative to ambient pressure within the suction channel 113.

The distal end of the suction channel 113 includes at least one flexible, resilient suction cup 121 disposed with a central axis thereof substantially orthogonal to the elongated axis of the suction channel 113. In an alternative embodiment, a suction cup 121 may be flexibly attached to the suction channel 113 for positioning and manipulating at selected angular orientations relative to an elongated axis of the cannula 111.

Figure 15A:
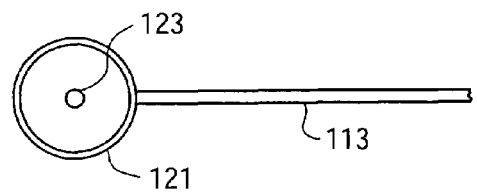
FIGS. 15a, 15b are, respectively, bottom and top views of the suction pod of FIG. 14.
Figure 15B:
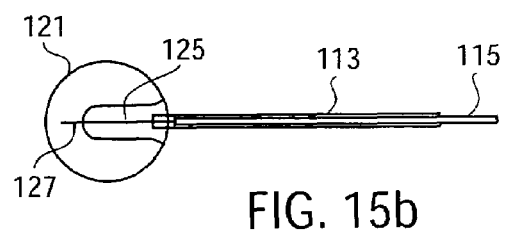

As illustrated in the bottom view of FIG. 15a, the interior recess of the suction cup 121 includes a suction port 123 in fluid communication with the suction channel 113. Also, as shown in the top view of FIG. 15b, the suction cup 121 may attach via a resilient, press-fit flange 125 onto the distal end of the inferior suction channel 113. The superior instrument channel 115 is illustrated in FIG. 15b as overlaying the flange 125, for example, to slidably support therein an ablation probe, for example, as previously described herein or an elongated, flexible needle 127 capable of delivering medications, injecting undifferentiated cells, installing electrical conductors, or the like, in a bodily organ such as the heart. Alternatively, the suction cup 121 may be attached via flexible coupling to the suction channel 113 and in fluid communication therewith to facilitate temporary suction attachment of the instrument to an organ such as the heart at any convenient angle of approach.

Figure 16:
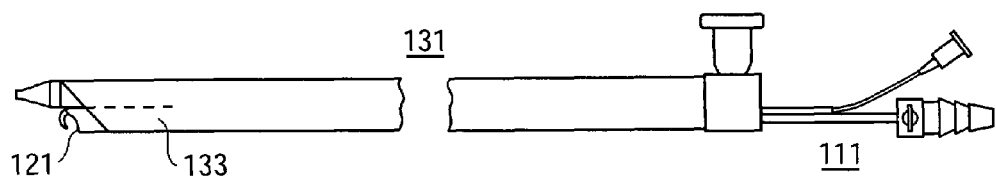
FIG. 16 is a plan view of a composite structure including a vacuum-assisted cannula slidably disposed within the endoscopic cannula.

Referring now to FIG. 16, there is shown a plan view of the assembled endoscopic cannula 131 and suction cannula 111 of FIG. 14, with the suction cannula 111 slidably disposed within the instrument channel 133 of the endoscopic cannula. Specifically, the resilient suction cup 121 may be curled or wrapped about the axis of the inferior suction channel 113 for slidable passage through the instrument channel 133. The resilient suction cup 121, once extended distally outside the instrument channel, resiliently expands to the undeformed cup shape to provide a large contact area of vacuum-assisted contact, for example, with the pericardium in or about the apex area of a patient's heart. The suction cup 121 may be re-coiled or re-wrapped about the axis of the inferior suction channel 113 for return to the instrument channel 133 of the subxiphoid endoscopic cannula in response to withdrawal or retraction of the inferior and superior channels 113, 115 back through the instrument channel 133, and in response to the peripheral edges of the suction cup 121 coming into contact with the angled distal edge of the instrument channel 133.

Mitral Valve Treatment

Figure 18:
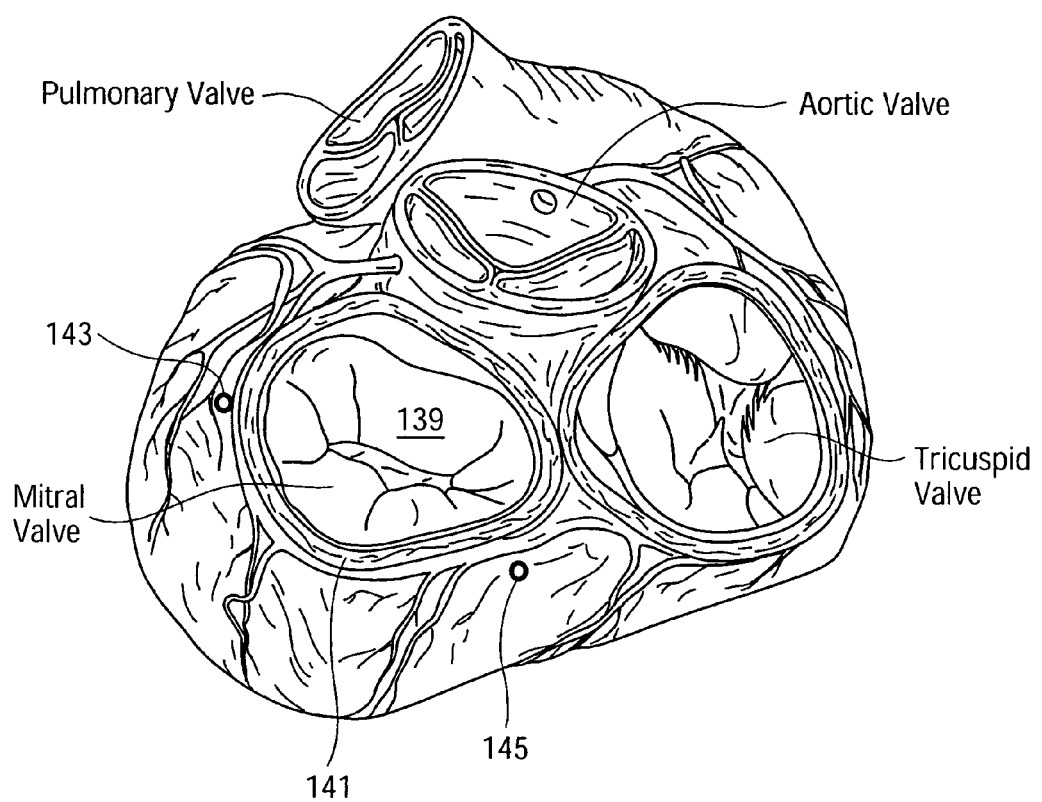
FIG. 18 is a partial top view of the heart showing the locations of epicardial tacks placed according to one embodiment of the surgical procedures of the present invention.
Figure 21:
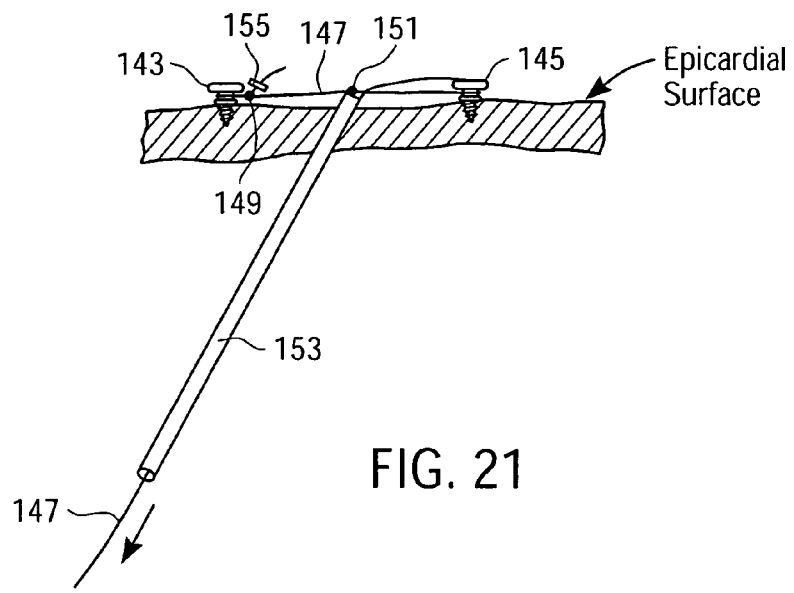
FIG. 21 is a plan view of FIG. 18 for installing the sutures of FIGS. 20a, 20b between epicardial tacks.
Figure 23A:
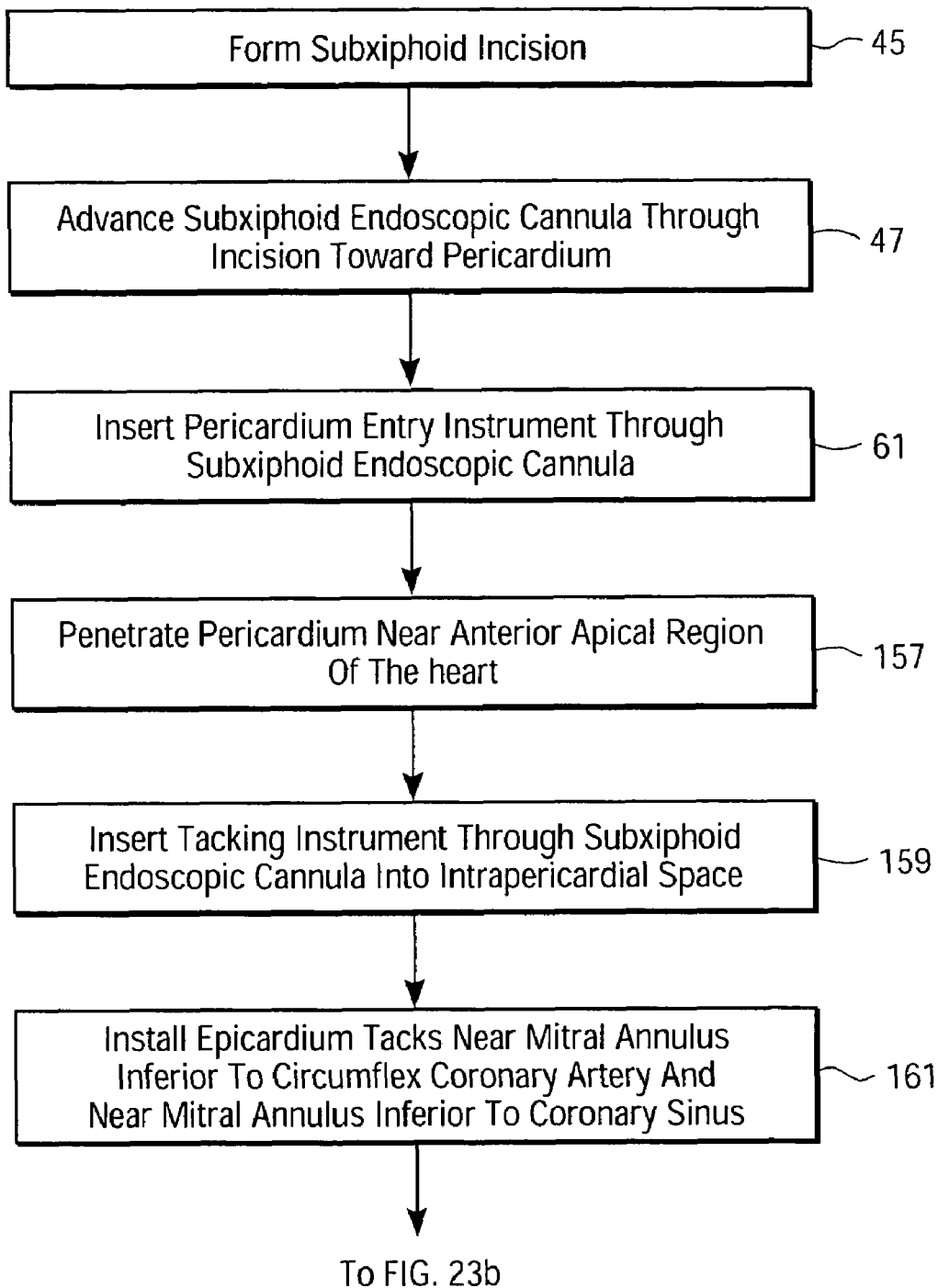
FIGS. 23a, 23b comprise a flow chart illustrating an embodiment of the surgical procedure in accordance with the present invention.
Figure 23B:
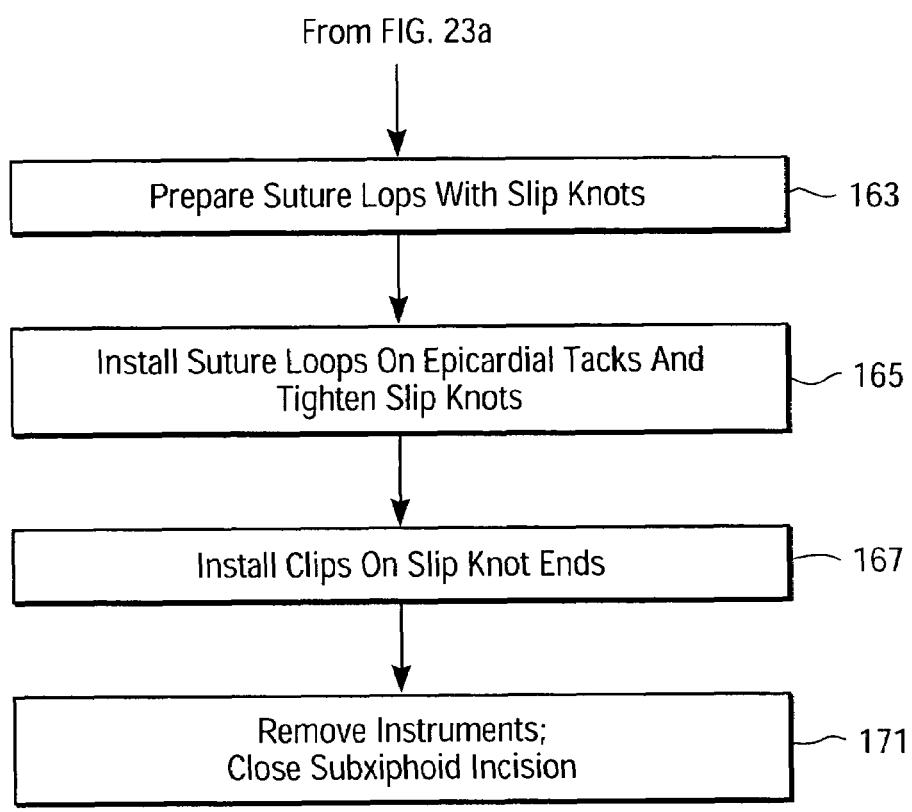

Referring now to the partial or cut-away top view of a human heart illustrated in FIG. 18, there is shown the mitral valve 139 and its annulus 141. The present invention can be used to change the size of the mitral valve annulus by placing tacks and tightening bands endoscopically on the exterior of the heart. One potential tack placement 143 is located inferior to the left circumflex artery in the anterior aspect of the mitral annulus, and another tack placement 145 is located inferior to the coronary sinus in the posterior aspect of the mitral annulus. FIG. 19 shows an anterior view of the heart, showing the tack 143 located inferior to the left circumflex coronary artery. A conventional tack applier (e.g., the TACKER previously available from Origin Medsystems, Inc., or the PROTACK available from U.S. Surgical) may be introduced through the endoscopic subxiphoid cannula, as previously described herein, for example, with reference to steps 45, 47 and 61 of FIG. 8a as illustrated in the flow chart of FIGS. 23a, 23b, entry through the pericardium is performed by the pericardial entry instrument that is inserted 61 via the operating channel of the endoscopic subxiphoid cannula and the pericardium is penetrated 157, as previously described herein, in the anterior pericardial surface near the apex of the heart. Following pericardial entry, the pericardial entry instrument is removed, and the tack applier shaft is advanced 159 through the operating channel of the endoscopic subxiphoid cannula to apply tacks 161 at the locations 143, 145 shown in FIGS. 23a, 23b. A looped suture or wire 147 is prepared 163 for tensioning of the epicardium by placement 165 onto the tacks, and by applying the desired amount of tension. The tack applier is then removed, and an endoscopic grasper is used to apply the looped suture or wire strand 147 to the epicardial tacks 143, 145.

Referring also to FIGS. 20a and 20b, there is shown an embodiment of a tension suture. Two loops are formed in a strand 147 of suture, with a slipknot 149, 151 formed at the base of each loop. The free end of each loop may be threaded through an axially rigid tube 153. The tube 153 functions as a knot pusher to close down on each loop, thereby shortening the distance between the two loops. In use, one loop may be placed on an inserted tack 143 and tightened down. The second loop is placed on the second tack 145 and the tail on the second loop is pulled through the tube 153 to shorten the loop and apply tension between the two tacks. At the desired amount of tension, vascular clips 155 are placed (step 167 of FIG. 23b) at the base of each suture tail to prevent the slipknots 149, 151 from slipping, thereby preserving the tension between the tacks 143, 145.

Figure 22:
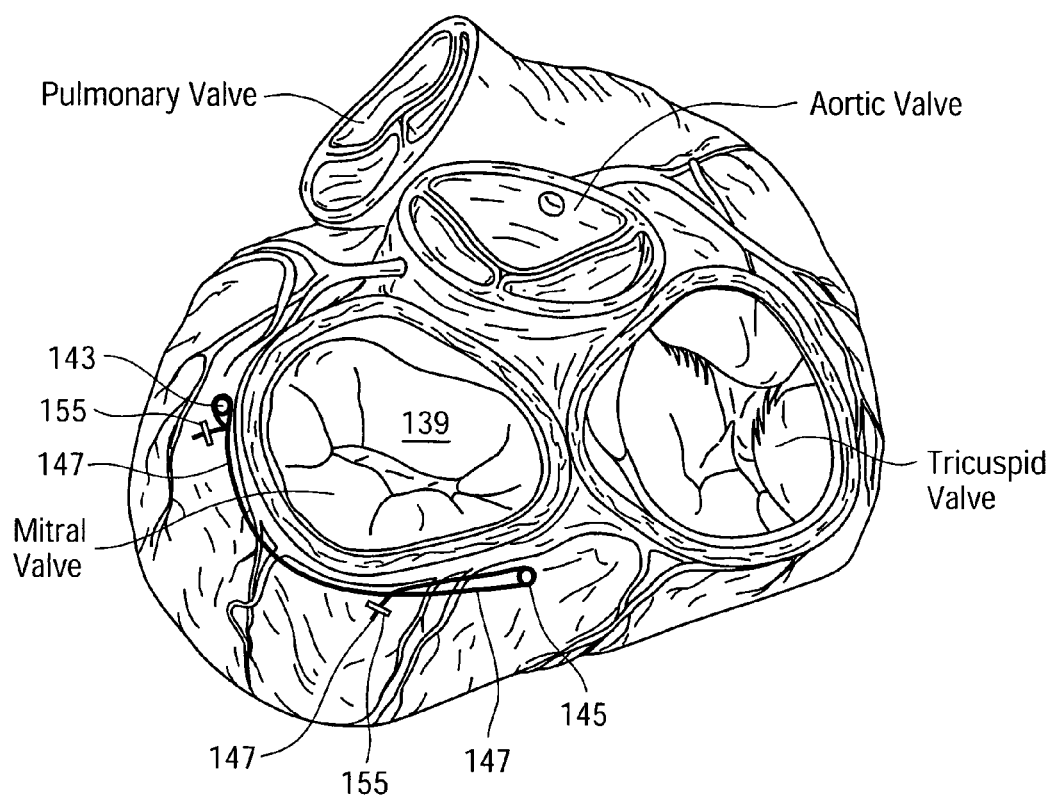
FIG. 22 is a partial top view of the heart showing the position of the suture loop between epicardial tacks.

FIG. 22 shows the anterior tack 143 and a posterior tack 145 in place with a length of suture 147 looped and tightened down on the anterior tack 143. A suture loop extends around the posterior tack 145 and the loop is tightened down and drawn toward the anterior tack 143 to the desired tension. Vascular clips 155 are placed on the suture tails adjacent the respective slipknots 149, 151 and the suture tails are then trimmed short to complete the mitral valvular repair.

In other embodiments of the present invention, a band or belt may be tensioned between anterior and posterior tacks 143, 145 to avoid cutting into the epicardium. Also, additional tacks may be installed in the epicardium at locations about the mitral annulus intermediate the anterior and posterior tacks 143, 145 to facilitate segmented tensioning of sutures or bands or belts from tack to tack about the mitral annulus. Thereafter, the instruments are removed from the body and the subxiphoid incision is closed 171 to complete the procedure.

Therefore, ablation of cardiac tissue within the intrapericardial space substantially surrounding the four pulmonary veins as a treatment for chronic atrial fibrillation is greatly facilitated by a tissue-ablating probe, or probes, of the present invention inserted along a tissue-dissected path and manipulated through an endoscopic cannula that is introduced along a dissected working channel from a subxiphoid or intercostal incision. Suction-oriented instruments facilitate temporary attatchment of an elongated body having a working channel therethrough to implement surgical procedures on the suction-attached organ at precise locations thereon. In addition, the subxiphoid access to the intrapericardial space facilitates placing epicardial tacks about the annulus of the mitral valve for tensioning the epicardium between tacks to decrease the size of the mitral valve annulus as a repair of a regurgitant valve.

What is claimed is:

1. A surgical procedure comprising:

forming an incision;

advancing an endoscopic cannula through the incision toward a target location on a patient's pericardium;

introducing a pericardium-penetrating instrument through the endoscopic cannula into contact with the pericardium at the target location;

forming an aperture through the pericardium at the target site to expose epicardial tissue;

introducing a tacking instrument through the endoscopic cannula through the aperture in the pericardium for installing a plural number of tacks at selected locations in the epicardial tissue including one epicardial tack at a region of the mitral annulus below the circumflex coronary artery, and another epicardial tack at a region of the mitral annulus below the coronary sinus; and installing an element in contact with at least a pair of the plural number of tacks to exert tension therebetween.

2. A surgical procedure comprising:

forming an incision;

advancing an endoscopic cannula through the incision toward a target location on a patient's pericardium;

introducing a pericardium-penetrating instrument through the endoscopic cannula into contact with the pericardium at the target location;

forming an aperture through the pericardium at the target site to expose epicardial tissue;

introducing a tacking instrument through the endoscopic cannula through the aperture in the pericardium for installing a plural number of tacks at selected locations in the epicardial tissue;

installing an element in contact with at least a pair of the plural number of tacks to exert tension therebetween including:

assembling a suture with a pair of loops formed with slip knots having trailing suture ends at spaced locations along the length of the suture;

positioning one of the pair of loops of the suture about one of the plural number of installed epicardial tacks;

positioning another of the pair of loops of the suture about another of the plural number of installed epicardial tacks;

advancing an elongated hollow tube along a trailing suture end from a slip knot for engagement thereof with a distal end of the tube; and pulling on the trailing suture end relative to the tube to selectively decrease a suture loop about an installed epicardial tack for tensioning the trailing suture ends to tension the suture between the pair of loops disposed about the installed epicardial tacks.

3. The surgical procedure according to claim 1 including:

installing an additional number of epicardial tacks intermediate said one and another tacks; and installing elements in tension between at least pairs of the number of installed epicardial tacks.

* * * * *

UNITED STATES PATENT AND TRADEMARK OFFICE
CERTIFICATE OF CORRECTION

PATENT NO. : 7,264,587 B2  
APPLICATION NO. : 10/346663  
DATED : September 4, 2007  
INVENTOR(S) : Albert K. Chin Page 1 of 1

It is certified that error appears in the above-identified patent and that said Letters Patent is hereby corrected as shown below:

Title page 2, under References Cited, patent number 3,338,916 should be 3,336,916.

Signed and Sealed this

Third Day of November, 2009

David J. Kappos  
*Director of the United States Patent and Trademark Office*